United States Patent [19]

Smith

[11] Patent Number: 5,512,467
[45] Date of Patent: Apr. 30, 1996

[54] ACYL-PEPTIDE HYDROLASE AND METHODS OF PRODUCTION AND USE

[75] Inventor: John A. Smith, Brookline, Mass.

[73] Assignee: The General Hospital Corporation, Boston, Mass.

[21] Appl. No.: 91,445

[22] Filed: Jul. 15, 1993

Related U.S. Application Data

[60] Division of Ser. No. 429,935, Nov. 1, 1989, Pat. No. 5,268,267, which is a continuation-in-part of Ser. No. 296,996, Jan. 13, 1989, abandoned, which is a continuation-in-part of Ser. No. 87,936, Aug. 21, 1987, abandoned.

[51] Int. Cl.$^6$ .......................... C12N 15/57; C12N 15/63; C12N 1/21; C12N 5/10
[52] U.S. Cl. ...................... 435/172.3; 435/240.2; 435/252.3; 435/212; 435/320.1; 435/254.2; 536/23.2
[58] Field of Search ................. 536/23.2; 435/320.1, 435/240.2, 252.3, 255, 69.1, 212, 172.3

[56] References Cited

U.S. PATENT DOCUMENTS

| | | | |
|---|---|---|---|
| 4,339,534 | 7/1982 | Johansen et al. | 435/70 |
| 4,438,032 | 3/1984 | Golde et al. | 260/112 R |
| 4,601,980 | 7/1986 | Goeddel et al. | 435/70 |
| 4,623,619 | 11/1986 | Owerbach et al. | 435/6 |
| 4,675,285 | 6/1987 | Clark et al. | 435/6 |
| 4,683,195 | 7/1987 | Mullis et al. | 435/6 |
| 4,879,214 | 11/1989 | Kornher et al. | 435/91 |

FOREIGN PATENT DOCUMENTS

| | | |
|---|---|---|
| 0200362 | 12/1986 | European Pat. Off. . |
| 0293266 | 11/1988 | European Pat. Off. . |
| 0303997 | 2/1989 | European Pat. Off. . |

OTHER PUBLICATIONS

Davis et al. in "Basic Methods in Molecular Biolosy" Elsevier, New York (1986) pp. 168–189.
Watson in "Molecular Biology of the Gene" The Benjamin/Cummings Publishing Co., Inc., Menlo Park, CA. (1976), p. 313.
Matsuda et al. (1981) FEBS Letters 126, 111–113.
Jay et al. (1983) Nuc. Acids Res. 11, 2325–2335.
Ullrich et al. (1984) EMBO J. 3, 361–364.
Lathe (1985) J. Mol. Biol. 183, 1–12.
Alwine, James C. et al., "Detection of Specific RNAs or Specific Fragments of DNA by Fractionation in Gels and Transfer to Diazobenzyloxymethyl Paper", Meth. Enzymol. 68:220–242 (1979).
Brauch, Hiltrud et al., "Molecular Analysis of the Short Arm of Chromosome 3 in Small–Cell and Non–Small–Cell Carcinoma of the Lung", New Eng. J. Med. 317(18):1109–1113 (1987).
Gade, Wayne et al., "Purification, Characterization and Possible Function of α–N–Acylamino Acid Hydrolase from Bovine Liver", Biochim. Biophys. Acta 662:86–93 (1981).
Gerber, Michael J. et al., "Regional Localization of Chromosome 3–Specific DNA Fragments by Using a Hybrid Cell Deletion Mapping Panel", Am. J. Hum. Genet. 43:442–451

(1988).
Jones, Wanda M. et al., "Acylpeptide Hydrolase Activity from Erythrocytes", Biochem. Biophys. Res. Comm. 126(2):933–940 (Jan. 31, 1985).
Klibanov, Alexander M., "Unconventional Catalytic Properties of Conventional Enzymes: Application in Organic Chemistry", in Basic Biology of New Developments in Biotechnology, A. Hallaender (ed.), 1973 [pp. 497–518].
Kobayashi, Kazumi et al., "Acyl–Peptide Hydrolase from Rat Liver", J. Biol. Chem. 262(24):11435–11445 (Aug. 25, 1987).
Kobayashi, Kazumi et al., "Cloning and Sequence Analysis of a Rat Liver cDNA Encoding Acyl–Peptide Hydrolase", J. Biol. Chem. 264(15):8892–8899 (May 25, 1989).
Kok, Klaas et al., "Deletion of a DNA Sequence at the Chromosomal Region 3p21 in All Major Types of Lung Cancer", Nature 330:578–581 (Dec. 10, 1987).
Lin, L–W et al., "Structural Organization of the Rat Acyl–Peptide Hydrolase Gene", FASEB J. 2:A999, Abstract 4086 (1988).
Marks, Neville et al., "Observations on N$^\alpha$–Deacetylation of Model Amino Acids and Peptides: Distribution and Purification of a Specific N–Acyl Amino Acid Releasing Enzyme in Rat Brain", J. Neurochem. 41:201–208 (1983).
Minna, John D., "Neoplasms of the Lung", in Harrison's Principles of Internal Medicine, E. Braunwald et al. (eds.), 1987 [pp. 1115–1123].
Naylor, S. L. et al., "The DNF15S2 Locus at 3p21 Is Transcribed in Normal Lung and Small Cell Lung Cancer", Genomics 4:355–361 (1989).
Pugniére, M. et al., "Peptide and Ester Synthesis in Organic Solvents Catalyzed by Seryl Proteases Linked to Alumina", Proteins: Structure, Function, and Genetics 1:134:138 (1986).
Suggs, Sidney V. et al., "Use of Synthetic Oligonucleotides as Hybridization Probes: Isolation of Cloned cDNA Sequences for Human $\beta_2$–Microglobulin", PNAS USA 78(11):6613–6617 (Nov. 1981).
Tsunasawa, Susumu et al., "Amino–Terminal Acetylation of Proteins: An Overview", Meth. Enzymol. 106:165–170 (1984).
Tsunasawa, Susumu et al., "Apparent Dipeptidyl Peptidase Activities of Acylamino Acid–Releasing Enzymes", J. Biochem. 93:1217–1220 (1983).

(List continued on next page.)

Primary Examiner—Robert A. Wax
Assistant Examiner—Rebecca Prouty
Attorney, Agent, or Firm—Sterne, Kessler, Goldstein & Fox

[57] ABSTRACT

The invention discloses the amino acid sequence of Acyl-Peptide Hydrolase. The invention relates to a DNA molecule encoded for Acyl-Peptide Hydrolase, a vector incorporating the molecule, and the use of such vector to transform a host. The invention further relates to the expression by the host to produce Acyl-Peptide Hydrolase, and the use of APH to catalyze the hydrolysis of an N$^\alpha$-acetylated peptide or protein or the reaction between an N$^\alpha$-acetyl amino acid donor and an acceptor protein with a free α-NH$_2$ group. The invention further relates to the use of the Acyl-Peptide Hydrolase-encoding sequences in the detection of cancer.

13 Claims, 23 Drawing Sheets

OTHER PUBLICATIONS

Tsunasawa, Susumu et al., "Purification and Properties of Acylamino Acid–Releasing Enzyme from Rat Liver", *J. Biochem.* 77:89–102 (1975).

Uradal, David L. et al., "Purification and Chemical Characterization of the Receptor for Interleukin 2 from Activated Human T Lymphocytes and from a Human T–Cell Lymphoma Cell Line", *PNAS USA* 81:6481–6485 (Oct. 1984).

Wood, William I. et al., "Base Composition–Independent Hybridization in Tetramethylammonium Chloride: A Method for Oligonucleotide Screening of Highly Complex Gene Libraries", *PNAS USA* 82:1585–1588 (Mar. 1985).

Yokota, Jun et al., "Loss of Heterozygosity On Chromosomes 3, 13, and 17 in Small–Cell Carcinoma and On Chromosome 3 in Adenocarcinoma of the Lung", *PNAS USA* 84:9252–9256 (Dec. 1987).

Zaks, Aleksey et al., "Enzyme–Catalyzed Processes in Organic Solvents", *PNAS USA* 82:3192–3196 (May 1985).

Zaks, Aleksey et al., "Substrate Specificity of Enzymes in Organic Solvents vs. Water Is Reversed", *J. Am. Chem. Soc.* 108:2767–2768 (1986).

```
                                                              60
MERQVLLSEPQEAAAALYRGLSRQPSLSAACLGPEVTTQYGGLYRTVHTEWTQRDLERMEN
|—CB17-R13——|   |——CB16-R18,19-C———————————|———CB17-R3—|
???????????????????????????????????????????????????
                                                              120
IRFCRQYLVFHDGDSVVFAGPAGNSVETRGELLSRESPSGTMKAVLRKAGGTVSGEEKQF
                                                              *
      |————CB/R97————|                        |———CB/R96————
      ??????????????????????                  ????????????? ??
                                                              180
LEVWEKNRKLKSFNLSALEKHGPVYEDDCFGCLSWSHSETHLLYVAEKKRPKAESFFQTK
           |—CB17-R33—|                                  |—CB16-R5—|
  ???      ????????????                                  ????? ??
                                                              240
ALDISASDDEMARPKKPDQAIKGDQFVFYEDWGETMVSKSIPVLCVLDIDSGNISVLEGV

300
PENVSPGQAFWAPGDTGVVFVGWWHEPFRLGIRYCTNRRSALYYVDLSGGKCELLSDGSL
                                                     *
                                       |———CB/R109————————
                                       ???????????? ????????
```

FIG. 1A

```
                                                      360
            320                    340
AICSPRLSPDQCRIVYLQYPCLAPHHQCSQLCLYDWYTKVTSVVVDIVPRQLGESFSGIY
|————|
  ??

420
            380                    400
CSLLPLGCWSADSQRVVFDSAQRSRQDLFAVDTQTGSITSLTAAGSAGSWKLLTIDKDLM
                              |————CB/R101————|
                              ???????????? ???????

480
            440                    460
VAQFSTPSLPPSLKVGFLPPPGKEQSVSWVSLEEAEPIPGIHWGVRVLHPPPDQENVQYA
             |————CB18-R15————|                 |—CB18-R11-13-c
             *  ????? ????? ?????? ?            ?? ????????????
                                                          ?? ??
                                                    |—CB18-R11-13-b
                                                     ?? ??

540
            500                    520
DLDFEAILLQPSNPPDKTQVPMVMPHGGPHSSFVTAWMLFPAMLCKMGFAVLLVNYRGS
|————|                                           |—CB19-R12——|
?? ???????                                        ????? ?  ?  ??

|—|
                                                                     ?

FIG. 1B
```

Figure 1C:
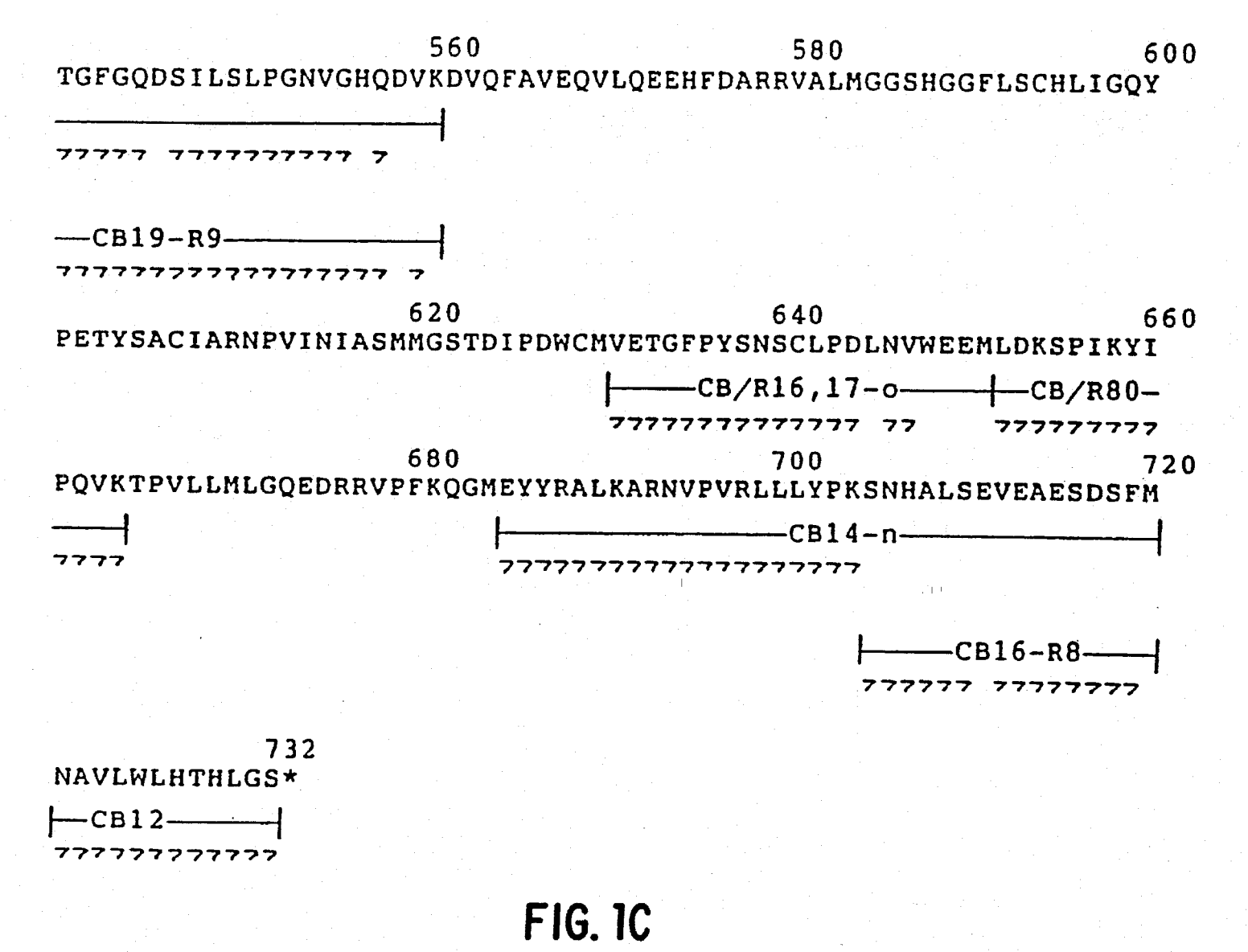

```
                560                     580                      600
TGFGQDSILSLPGNVGHQDVKDVQFAVEQVLQEEHFDARRVALMGGSHGGFLSCHLIGQY
?????? ?????? ?
    CB19-R9
?????????????????? ?
              620                      640                      660
PETYSACIARNPVINIASMMGSTDIPDWCMVETGFPYSNSCLPDLNVWEEMLDKSPIKYI
                                        CB/R16,17-o      CB/R80
                                 ?????????????? ??       ???????
              680                      700                      720
PQVKTPVLLMLGQEDRRVPFKQGMEYYRALKARNVPVRLLYPKSNHALSEVEAESDSFM
                                             CB14-n              CB16-R8
????                                 ??????????????????        ?????????

732
NAVLWLHTHLGS*
  CB12
??????????
```

Val-Leu-His-Pro-Pro-Asp-Gln-Glu-Asn-Val-Gln-Tyr-Ala-Asp-Leu-Asp-Phe-Glu-Ala-Ile-Leu-Leu-Gln-
GTG-CTA-CAC-CCA-CCT-GAC-CAA-GAG-AAT-GTA-CAA-TAT-GCT-GAC-CTT-GAC-TTT-GAA-GCA-ATC-CTT-TTG-CAG-

```
1    CGACTATGGAGCGTCAGGTGCTGCTGAGTGAGCCCCAGGAGGCGGCAGCGCTGTACCGGG    60
     M  E  R  Q  V  L  L  S  E  P  Q  E  A  A  A  L  Y  R  G

61   GCCTTAGCCGCCAGCCTTCGCTGAGCGCCGCCCTGGCTCCGGAGGTCACCACGCAGT     120
     L  S  R  Q  P  S  L  S  A  A  C  L  G  P  E  V  T  T  Q  Y

121  ATGGGGGCCTCTATCGGACCGTGCACACTGAGTGGACTCAGAGGGACTTGGAGCGAATGG    180
     G  G  L  Y  R  T  V  H  T  E  V  T  Q  R  D  L  E  R  M  E

181  AGAACATCCGATTCTGCCGCCAGTACCTAGTGTTTCATGACGGTGGTGATTCGGTGTTTG    240
     N  I  R  F  C  R  Q  Y  L  V  F  H  D  G  G  D  S  V  V  F  A

241  CCGGGCCTGCAGGCAACAGTGTGGAAACCCGGGGAGCTGCTGAGCAGTCTCAGGAGTCTCCTT    300
     G  P  A  G  N  S  V  E  T  R  G  E  L  L  S  R  E  S  P  S

301  CAGGCACCATGAAAGCTGTGCTTCGCAAGGCCGGAGGCACAGTCTCAGGAGAGAAAAC    360
     G  T  M  K  A  V  L  R  K  A  G  G  T  V  S  G  E  E  K  Q

361  AGTTCTTGGAGGTCTGGGAGAAGAACCGGAAGCTCAAGAGTTTCAACCTGTCAGCCTGG    420
     F  L  E  V  W  E  K  N  R  K  L  K  S  F  N  L  S  A  L  E

421  AGAAGCATGAAGGGCCTGTCTATGAGGATGACTGCTTTGGCTGCCTTTCCGTCACACTCAG    480
     K  H  G  P  V  Y  E  D  D  C  F  G  C  L  S  V  S  H  S  E

481  AGACACACTTGTGTATGTGGCGGAGAAGAAGCGTCCCAAGGCTCCGAGTCCTTCTTTCAGA    540
     T  H  L  Y  V  A  E  K  K  R  P  K  A  E  S  F  F  Q  T

541  CCAAAGCCTTGGACATCAGTGCCAGCGATGATGAGATGGCCAGGCCGAAGAAGCCAGACC    600
     K  A  L  D  I  S  A  S  D  D  E  M  A  R  P  K  P  D  Q
```

FIG. 3a

```
601  AGGCCATCAAGGGGGACCAGTTTGTATTTTATGAAGACTGGGGAGAAACGATGGTTTCCA  660
      A  I  K  G  D  Q  F  V  F  Y  E  D  W  G  E  T  M  V  S  K
661  AAAGCATCCCTGTGCTCTGCGTGCTAGATATCGACAGTGGCAACATCTCTGTGCTTGAGG  720
      S  I  P  V  L  C  V  L  D  I  D  S  G  N  I  S  V  L  E  G
721  GAGTCCCTGAAAATGTGTCACCTGGTCAGGCTTTTTGGGCCCCTGGAGACACGGGGGTGG  780
      V  P  E  N  V  S  P  G  Q  A  F  W  A  P  G  D  T  G  V  V
781  TGTTTGTGGGCTGGTGGCATGAACCCTTCAGGCTCGGCATCCGCTATTGCACCAATCGCA  840
      F  V  G  W  W  H  E  P  F  R  L  G  I  R  Y  C  T  N  R  R
841  GATCAGCTCTGTACTATGTGGACCTGAGCGGGAAGTGTGAACTACTCTCGGATGGTT    900
      S  A  L  Y  Y  V  D  L  S  G  K  C  E  L  L  S  D  G  S
901  CCCTGGCCATCTGTTCCTCCCGGCTCAGCCCCAGACCAGTGTCGCCATCGTCTACCTACAGT  960
      L  A  I  C  S  P  R  L  S  P  D  Q  C  R  I  V  Y  L  Q  Y
961  ATCCATGTCTAGCCCCTCATCACCAATGCAGCCAGCTCTGCCTGTACGACTGGTACACCA  1020
      P  C  L  A  P  H  H  Q  C  S  Q  L  C  L  Y  D  W  Y  T  K
1021 AGGTCACCTCAGTGGTGGACATTGTACCCCGGCAGCTGGGAGAGAGCTTCTCTGGAA    1080
      V  T  S  V  V  D  I  V  P  R  Q  L  G  E  S  F  S  G  I
1081 TCTACTGCAGTCTTCTTCCTTTGGGATGCTGGTCAGCTGACAGCCAGAGAGTAGTCTTTG  1140
      Y  C  S  L  L  P  L  G  C  W  S  A  D  S  Q  R  V  V  F  D
1141 ACTCTGCCCAGCGGCAGTCGGCAGGACCTGTTTGCTGTGGACACCCAGACGGGCAGCATCA  1200
      S  A  Q  R  S  R  Q  D  L  F  A  V  D  T  Q  T  G  S  I  T
```

FIG. 3b

```
1201 CCTCCCTGACAGCTGCGGGGTCAGCAGGAAGCTGGAAGCTGCTTACAATTGACAAAGACC
       S  L  T  A  A  G  S  A  G  S  W  K  L  L  T  I  D  K  D  L

1261 TTATGGTTGCCCAGTTCTCCACACCCAGTTGCCCCAAGCCTGAAAGTTGGGTTCCTGC
       M  V  A  Q  F  S  T  P  S  L  P  P  S  L  K  V  G  F  L  P

1321 CTCCTCCTGGGAAGGAGCAGTCTGTGTCATGGGTGTCCCTGGAGGAGCTGAACCTATTC
       P  P  P  G  K  E  Q  S  V  S  W  V  S  L  E  E  A  E  P  I  P

1381 CTGGCATCCACTGGGGCGTCCGTGTGCTACACCCACCTCCAGACCAAGAGAATGTACAAT
       G  I  H  W  G  V  R  V  L  H  P  P  D  Q  E  N  V  Q  Y

1441 ATGCTGACCTTTGACTTTGAAGCAATCCTTTTGCAGCCCAGCAATCCTCCAGATAAGACCC
       A  D  L  D  F  E  A  I  L  L  Q  P  S  N  P  P  D  K  T  Q

1501 AGGTCCCCATGGTAGTCATGCCCCATGGGGACCCCCATTCGTCCTTCGTCACTGCCCTGGA
       V  P  M  V  V  M  P  H  G  G  P  H  S  S  F  V  T  A  V  H

1561 TGCTGTTCCCAGCCATGCTCTGCAAGATGGGCTTTGCAGTACTTCTGGTGAACTATCGTG
       L  F  P  A  M  L  C  K  M  G  F  A  V  L  L  V  N  Y  R  G

1621 GCTCCACTGGCTTTGGCCAAGACAGCATCCTTTCTCTCCCAGGCAATGTGGGCCACCAGG
       S  T  G  F  G  Q  D  S  I  L  S  L  P  G  N  V  G  H  Q  D

1681 ATGTGAAGGATGTCCAGTTTGCAGTGGAGCAGGTACTCCAGGAGGAACACTTTGATGCAA
       V  K  D  V  Q  F  A  V  E  Q  V  L  Q  E  E  H  F  D  A  R

1741 GACGCGTGGCCCTTATGGGTGGTTCCCATGGTGGTTTCCTCTCCTGCCACCTGATTGGTC
       R  V  A  L  M  G  G  S  H  G  G  F  L  S  C  H  L  I  G  Q
```

FIG. 3c

```
1801  AATACCCGGAGACCTACAGTGCTTGTATAGCCCAGTGATCAACATTGCCTCCA  1860
       Y  P  E  T  Y  S  A  C  I  A  R  N  P  V  I  N  I  A  S  M
1861  TGATGGGCTCCACTGACATCCCTGATTGGTGTGTATGGTGGAGACTGGCTTCCCTTATAGCA  1920
       M  G  S  T  D  I  P  D  V  C  M  V  E  T  G  F  P  Y  S  N
1921  ACAGCTGCCTCCCAGATCTGAATGTGTGGGAGGAGATGCTGGATAAGTCACCCATCAAAT  1980
       S  C  L  P  D  L  N  V  V  E  E  M  L  D  K  S  P  I  K  Y
1981  ACATCCCTCAGGTAAAGACACCAGTGTTACTGATGCTGGGCCAGGAGGACCGACGGGTAC  2040
       I  P  Q  V  K  T  P  V  L  L  M  L  G  Q  E  D  R  R  V  P
2041  CCTTCAAGCAGGGTATGGAGTATTACCGTGCCCTCAAGGCCCGGAATGTGCCTGTCCGGC  2100
       F  K  Q  G  M  E  Y  Y  R  A  L  K  A  R  N  V  P  V  R  L
2101  TCCTGCTGTACCCCAAGAGCAACCACGCTCTGTCAGAGGTGGAGGCGAGTCAGACAGCT  2160
       L  L  Y  P  K  S  N  H  A  L  S  E  V  E  A  E  S  D  S  F
2161  TCATGAACGCTGTGCTTTGGCTTGCACACACACTTGGGCAGCTGAAGCCCTATGTTCTTCT  2220
       M  N  A  V  L  W  L  H  T  H  L  G  S  *
2221  TGAGCTGGGCAGCCCGTCTTGCACTTTGCTCTTGGTAAGCTCCAGGATCTGACCGAACAG  2280
2281  CCAAACAGTCTCCTAGGCTGTGGACTCAGTGAATGGGCAGAGGACTAAGAACTATGTTAT  2340
2341  CATAATAAAGGAAGACACAGAAAAAAAAAAAAAAAAAAAA  2381
```

```
1380  ctccctgtactgtgacaagtgtattctgtggtatcagaatataaaggacttgatataaacaacctccagactgtcttgg
1300  gatgatttctgaagtgggaatgcttagccaaacaagtaaatgccaatgcttgtgacaatatcctcaatgattaaagacga
1220  gagagagagagagagagagagagagagagagaaacaacgtttcagaaatgtggtacacaactgggct
1140  aagtttaaaaatgattgtccaggaagtgtaaaggcctgtccccaccaatgggtttccaccagttttcagggttctggt
1060  tcccaggagctagtgctgccccctggtgctctccaagcaagctttacatttgtctgccttgctccaacctcagaatcctcc
-980  ccccccccaggctaagaccttaattcccacatatagtccaagaccggtgtcatagcccacacttt
-900  tttaaaaagattattatcatataagtacactataccagtcttcagacacaccagagagtcagtgtctca
-820  ttacagtaggctgtgagccaccatgtggttgctgggatttgagctcaggacctctggaagagagcagtcagtgctgt
-740  actgagccatctctccagctcatagcccacactttttaaaattttattatttatgtatgacactgtagctgt
-660  cttcagacacaccagagagtgctctcaggatccattacagatggttgtgagccaccatgtggttgaactcaggacctct
-580  ggaagagcagtcagtgctctcaaccgctagtctagtcatctccagatcccaaagtccacattttaatccagctctt
-500  gggaggcagagataggtgggtctctgtgagttagaggccaggactatgtgagaaactaaacatataagtcaagtatca
-420  ctagaaataagaaacagagactaaacaagtgtatcaatttgcctcgggaagaaagaaagtactcattcaagggac
-340  catagctggtctgaaagagcagccagtcctcaaggatatggaggaagggggatgcctactgttgccaacctctcttgcc
-260  ctctgctgtcacctagttcaacctagtcctgtgtggtgcaagaggagaccgcctgtctaggctcttctcttccactgc
```

FIG. 4a-1

```
  80  acctcgctgctcttccgtgaagtctgaccccacccacatctgctcttggagtgggctgactcagtctgctcaagatcagc
 100  atcaatgagtcactgaaaagggcgggttaaggctgtagcaacagatagcttcggggcaagtctgttgataaaccg
 220  gggtagcacccagagagttcAGCACCGCCCTTTGCCCCGGCCCCGGGACCTGCCCGGGACCTGATTTTCTCACTCCTA
 161  ACCGCCTGGCTTGCAGTAAATGCGGAGTAAATGCGGAGAGAGTCAAAGAGATCCCTGCGAGTGCCGCGCCCCAACGTTTGACTTCAT
 141  GGACCTTTCCCACCCCACCCCAAATCCCCTGTCCCTCATCCTTCAGGATCATTGGCGTTCCTCTTAAGCACAGCCCTTC
                                                                  |---intron 1
 221  GAATGAATACTCAGAGTTTCTCTCTGACCCGCAGCTCACAgtcggctgaagtccgtcctactcttcactcatccc
 301  agacctccccatcccggaacaccagctctgttttctgcggttacatttctgccctcgctcctcggaggctttcccctct
 381  ctaaaaatcccaggaccgactcccaggttctgcctcccgactgcaatcccgctccttccgagctcttcgtagccc
                                             ---|
 461  cgccttcataccaccagcaccgccccagCTGGTTGGGCCCCGAGCTTTGCTGGGCCTCACTTCCGGACTTAGGCGTACAGAAAGATC
                                |---intron 2
 541  GGGTGTAGCGGGAAACTGGGACGCCTTCAGgtgagggtcggccgtggccctggctccgtagcccggctgagcctgacctgtgtc
                                   ---|
 621  GACTATGGAGCGTCAGgtgagggtcggccgtggccctggctccgtagcccggctgagcctgacctgtgtc
 701  ccctgcgcagGTGCTGCTCCGGAGCTGAGTGCTGAGTGCTGCTCCGGAGCCCCAGGCCGTGTACCGGCGGCCCTTAGCCCGGGCCGGCCTTCGCTGAGCG
                                                                          |---intron 3
 781  CCGCCTGCCTGGGTCCGGGCAGGTCACCACGGCCTCTATGGGGCCTCTATGGACCGTGCACACTGgtgtgtagaccgagggg
 861  actgggtggcgacggccgtgcatccaggtggaaggcacgctgcttgacacggctgggaaccaa
 941  ctgtagttcctgcgcacaggtgtttgggggttgtggtagcccgtaaatgaattgaaagtgtgggagtaaattcagac
```

FIG. 4b

```
 021  ctgcatggaaggtgtgaacctcgcagacctctccaaccctacattctatagcccaacaacagttacgttgcccttaaaa
 101  ttctatggttggtagtgggttctctccgactgtcagctcaggctctggaaacctaggcttaggttatattagtgaagtgt
 181  tgaccaggtttactcaggatgtccgaagacagactggaaaaggtaggccatgattggtgggtagtgatcaaagtggcc
 261  cagacaagttgagcagctctgtgcctccctgcagAGTGGACTTCAGAGGGACTTGGAGCGAATGGAGAACATCCGATTCT
 341  GCCGCCAGTACCTAGTGTTTCATGACGGAGACTCGGTTGGTGTTTGCCGGGCCTGCAGGCAACAGTGTGGAAACCCGGGGG
      |---intron 4
 421  GAgtaagtgtgacaggagtttgtagatgagaacctccctgcagcaacttggtagcttcagaggagcaaagaaccaggtgc
 501  gtccttaggtgtcaagctctgtgccgctccccttcaggacaactttggtagcttcagaggagcttcttcctaactaggtctggt
 581  ctgctccttgagagtttatttggtctctggagacatggccagctgataaacactagaagcttcttcctaactaggtctggt
 661  ccctgggaatctgaagagtcacgtaaggaagagagagaaggccagctgcttgaggagtgtgcatggctgta
 741  tgagatcagactccagttagctgggagatgtctcccatgctgccctccgactttgtaatgctagaccaaaaaaaaa
 821  aaaaaaaaaagcttataaagaaagggagaggggctagagatagcacagaggttaaaggaccttttcagaggccgt
 901  gagttcaattccagcaaccacatggtgctcacaaccatctgtaatgagacgtgacgccctcttctggcctgcagtcac
 981  atatgcaggaatgctgtatatataataaataaatcttaaaagaaaaaggaagagagagagagagagaga
2061  gagagattcattcattcatgtaagaggctatgaccagtaaggggcagcacaaggctgttgggcttggcag
2141  aatcctgacctgaccccctgttctctcagGCTGCTGAGCCAGCAGAGTCCCTTCAGGCACCATGAAAGCTGTCTTCGCAAG
```

FIG. 4b-1

```
                                          |---intron 5
 21   GCCGAGGCACAGTCTCAGGAGAGGAAAAACAGTTCTTGGAGgtgagtctgcaaggacgaggtggcaggcagtaggcat
                                                                              |---|
 01   agtgaggaggatctgcggagggcaggcagcctgatatcccagGTCTGGGACAAGAACCGGAAGCTCAA
                                                                   |---intron 6
 31   GAGTTTCAACCTGTCAGCGCTGGAGAAGCATGGGCCTGTCTATGAGGATGgtgaggcctggctgtaagcaggcaggg
                                                       |---|
 51   tgggagagaagggcagcatagctttgggctccccctaatcgtccctcctgcatgtagACTGCTTTGGCTGCCTTTCCT
 41   GGTCACACTCAGAGACACTTGTGTATGTGGGAGAAGAAGCGTCCAAGGCTCAGTCCTTCTTCAGACCAAAGCC
                                                                   |---intron 7
 21   TTGGACATCAGTGCCAGCGATGATGAGATGGCCCAGGCCGAAGAAGCCAGCAGGCCATCAAGtgcttgtggtgtggcc
 01   aggccacgaaggcccgcgctgggcactgtatccagtggagccctgggaggcccgaatgtctaggaggcagg
                                                         |---|
 81   cagggttctgaaggcactgggcatggagctgtcctctgttctctgcagGGGGACCAGTTTGTATTTTATGAAGACTGGGAGAA
 61   ACGATGGTTTCCAAAAGCATCCCTGTCTGCTCTGCGTGCTAGATATCGACAGTGGCAACATCTCTGTCTTGAGGGAGTCCC
                                      |---intron 8
                                      |---|
 41   TGAAAATGTGTCACCTGGTCAGgtcagcagcaacttggcctgcctgtgcctcccgaggcagggttccctgtctgagcaattc
 21   gtcttgctcatacctactttggtcttgtcttacagGCTTTTTGGCCCCCTGGACACACGGGGGTGGTGTTTGTGGGCTG
                                                                     |---intron 9
                                                                     |---|
 01   GTGGCATGAACCCTTCAGGCTCGGCATCCGGCCATTGCACCAATCCAGgtgaggaaatgggaccagagggccgttat
 81   ggccagccgaccatggagctgagtgtctctctgacctttccagATCAGCTCTGTACTATGTGACCTGAGCGGAGGAA
      |---intron 10
      |---|
 61   GTGTGtaagtgtctggcgtccgcatgctgcctgacacatgtgcttagtcttccccgtgaatgtgtcagtcactca
 41   tatttctggcctagAACTACTTCTCGGATGGTTCCCTGCCATCTGTTCCTCCTCGGCTTCCTCAGCCCAGTGTCGCAT
```

FIG. 4c

```
                                                        |---intron 11
 21  CGTCTACCTACAGTATCCATGTCTAGCCCCCTCATCACCAATGCAGCCAGTCTGCCTGgtgagtggagggtgagggtga
 01  ggggtgtggtggttagcttcttgttgggaacgaaggctaaaggacatggtcatctcccccttgggcct
 81  ctcctgtcttcagtggatcagtggcttgaccttcaaggtagaccttgagcactctcggggctcacctctta
661  agagtctcctccagtcacttagttcacatctccaagaagccaggctctacaaggagcaggggcagagttggaggctatac
741  agagtccatccctgcacaaggagagccctgggtggaagtcaaggacacacctatctgagacaagtccaggctaccgta
821  aaagataaattagcccccttctctccctaaagcaatcaaagttgtcacctgaagagatagatatctgcgcctgaga
901  tccatgccctggtgggtctgaccattgtgttctcttgcagTACGACTGGTACACCAAGGTCACCTCAGTGGTGGACA
                                        |---intron 12
981  TTGTACCCCGGCAGCTGGGAGgtaagaggtgcctggctggctactgagccctgttgcccaggccaagatggtgc
061  ttcctgggttccttggaggactctctcctgctactgagtagccaagatcagagaagccccaccagagataagagatggtgc
141  tatgggtaatagcctgataagataagactgggctgggtgtggtttactctgtttcctgcccggcaacttgtcagtgtaagt
221  tgttagcttgagaagcactgggctgtgggtgtgtagctatgaggctccttacagctctgttgcagtc
301  gagctggtcctctggaaagggactcgaagctgttacagctctgcttcagtc
381  ctcgggcatccaaggactacatgcggaggaaaagtcttttctcaaaccaccgagaaaggtccaaggtcaagtcagtggggcaggtc
461  cagcagacaaagttccaggataaagcacatggctacctgtgcgtgatccttagcacatacccttgagtttgcaaggacac
541  cataataggacctagtctgaacctcagctgccattagctgtgtcctgtctgtcttcatgagctt
```

FIG. 4c-1

```
4621  ctgtttctccatttgtggacagggtgatcaagtccaccttctgagctcctgatgagctgctgtactctgcactctggtg
4701  gataagtacgttatcttaatacgggttaaggcacttacattgccaagaccaaaaggaatagccaatagaaagcatcg
4781  agttcgcaaataagctcaccagctctgcctcttccagtctgcctcagaaggttcccccaccccccttcaccttctactcag
4861  taaactcctcattgccaaaggtaccctcatgtctaggactatctacctcagatttcagggcctgggtgaattcccaa
4941  cttcatattctcgatccccaggcccctctaagatggcagcttacacccttctaccttgcagAGAGCTTCTCTGGAAT
5021  CTACTGCAGTCTTCTTCCTTTGGGATGCTGGTCAGCTGCTCACACCCAGAGAGTAGTCTTTGACTCTGCCCAGCGAGTCGGC
      |---intron 13
5101  AGgtaaaagcctctgattgtgtggagaggtagcatcaacatttgctgggcaaagtgagtatgtgccctaggaggatg
5181  ccgagcctgaaagtcttaactggctcccaagaagcctttttctgcctctgctgacttagtttcttaagaggaccaaat
5261  gttgggttgaggatttagctcagtggtagagcacttgcctaagcaaggcgcaaggccctgggttcggtcccccagctccga
5341  aaaaaaagaaaaaggaagaaggagaccaaatgttctgatggccccacagagagcccttgagggatgatgtgccggatgtgccatgg
5421  gggtccctgaacacttggtaatgcagttgatggagacaggatgggccccttgagggatgatgtgccggatgtgccatgg
5501  tcctttaggtatgatatttctgttcctcatatctttgttcctggattatctagtacttttgtgaaggaattgaat
5581  ctagatccagggttatccctgttttacacagtagccatcacgtagccaatgtccctaagacagtagaaaggacatcgg
5661  gctgttggatgtgctgctacaagtggtctccccactgtttaagGACCTGTTTGCTGTGGACACCCAGACGGGCAGCATCA
      |---intron 14
5741  CCTCCCTGACAGCTGgtgagcaggaccctctgcagtagggtggctggtgggtgggtggatggcagcttaggaaaagcgcta
```

FIG. 4d

```
5821  gagcttggttggcatggggcagcagtggtgctccacacgccctggcgtgctccacacccctgtcccacccctgtcctaaggtcacaga
5901  cctttcctgcaatctattgtagtcatccactcctgcccagacccttggagaaaccttgggtggactctctagcattcctg
5981  cactctcccctatggtctgcctcagaagcagccctttgagtcctccacgactggactctgcactctgcctatatctgct
6061  ttctctagggcggtcagcagggagctggaagacagaagatgctgtcttcgggtttccattgctgtgacgagacaccatg
6141  atcgtggctcctctcttaataaggagacatttaattggggctggcttacagatccagaggtttagtccgttattgtcatggc
6221  agggagcggggcagcgctcaggcagcagattggctggcagcagaaagacagtgacctagacctgacttgagcttctgaaacc
6301  tcaaagcccacctcaatggcgcactccttaacagcgcaccctcttaatagtgccactccctatgaggctactggg
6381  ggccatttttattcaaaccactacaggtgataagtcctaattctgcacctcattactagggtgtttccctagggtataca
6461  aagctcgtgcacataaataagtagtagtagtagtagcctaattcacgtaagtaatgacaataataaatgg
6541  agtagtagcagcagtaatacacaaagcctagtaaagcctaatcagttttttgggctgttcccttacgttgcagtctttga
6621  ataagctttagccagtccctctttcctccaccagttttttgggctgttcccttacgttgcagtctttga
6701  gtaaatagagtaccttggtagctttctgtgtcccagtctgtgcaattcttgagtataatcagtgtctctcagatgaaca
6781  ggaggcttaccaggacatgtgcagttaggtagtagaaaagtggccctgccaggcacttacatcatctgcttcctctagC
6861  GGGTCAGGAGGAAGCTGGAAGCTGCTTACAATTGACAAAGACCTTATGGTTGCCCAGTTCTCCACACCCAGTTTGCCCC
      |---intron 15
6941  CAAGCCCTGgtgagtattgtgggtctcaggctagagccgagccggattaacaagactccatgcgaactcgaagactg
```

FIG. 4d-1

```
7021  accgtgctggccagcatgtagaagggcagagaggacttggctccagctagtcctgtggttctttggctcgcactcaa
7101  gagtaggaactaggccagcacagtgtgcctacagaagtgccagtcatttattattagagtccaggaaacagaaaaac
7181  tagaagccaagaagaaatgtggtagggctaggggtggtccatatgtcagtgtcatatgcagtgctctgtagaaatg
7261  ggcttctgagagctggcccgcctgactttcctcccgttgcagAAAGTTGGGTTCCTGCCTCCTGGGAAGGAGC
7341  AGTCTGTGTCATGGGTGTCCCTGAGGAGGCTGAACCTATTCCTGGCATCCACTGGGGCCGTCCGTGTGCTACACCCACCT
              |---intron 16
7421  CCAGACCAAGAGAATGTACAATATGgtgagctgggccgatggcggggtggacggcttctccagacccacacacagatc
7501  tgtggcgacccttcctagctcacgttgaaggcttctctgaatttttctgatcttatggtcatgggga
7581  gtagcatccaaagatctgagtacctgctgtggttatcagcactggtcctgccaggcatatctctgtggtgagaaagt
7661  taagatttaaaggaagtaggcctctcccaggcttagggggcacaagctttaggggcacaagtgttatccttccagacaataggctctct
7741  gacaaggcagaaagggcacaagctttaggggcatgccatgggggagctgcctaggcgctacttggctggct
7821  ctgtttcacttgatcaggtttgtatcagacctgcagCTGACCTTGACTTTGAAGCAATCCTTTGCAGCCCAGCAATCCT
                                            |---intron 17
7901  CCAGATAAGACCCAGGTCCCCATGGTAGTCATGCCCCATGgtaggtatttacctaagagccctgccacctaccaccct
7981  cctagctggcctttcatggcctgtcgcttcctgtctgcagggagaaggcagtagcagcaagaccagtcctgctttccaaa
8061  ggcttccttagccaagtccatctgcagGGGACCCCATTCGTCCTTCGTCACTGCCTCGATGCTGTTCCCAGCCATGCT
                                  |---intron 18
8141  CTGCAAGATGGGCTTTGCAGTACTTCTGgtaagtcagaacgacctgcaattccactgggtccatgaagcgatgggt
```

FIG. 4e

```
8221  ggccttggttgtatatcctttctatggtgtacttactctttagaaacgggctgggcaatggggcacactcttttaatc
8301  ccagcacttagaaggcagaggcaggtgaagtttgagtccaaggatcatcaggactacacagaaaaacctgttttgaaaa
8381  caaaagaaactactagaaattgccctggcttagcctctggttcgtaacctggtgatcaggtggattaacttgaagc
8461  ttctgtggaaggatcctatggtctctgggtagcagcttcatctctctcttggctacctccccttgacagcacgtgatgcag
8541  ctggtcctagggcctatgtcacagcacatggaattgggtgggactgagaccattgcccaactatctgtctcacttt
      ¦--¦
8621  cagTGAACTATCGTGGCTCCACTGGCTTTGGCCAAGACACAGCATCCTTTCTCCCAGGCAATGTGGCCACCAGGATGTG
      ¦---intron 19
8701  AAGGATGTCCAGgttgcagggcggtgggctgctggacaggagggtggattcatggctttcggctgccagcgagcgaact
      ¦---¦
8781  gtagtgtcctctgcccacactttagTTTGCAGTGTGAGGAGCAGGTACTCCAGGAGGAACACTTTGATGCAAGACGGTGCCC
8861  TTATGGGTGGTTCCATGGTGGGTTCCTCTCCTGCCACCTGGTCAATACCCGAGACCTACAGTGCTTGTATAGCC
                                                                          ¦---intron 20.
8941  CGGAACCCAGTGATCAACATTGCCTCCCATGATGGGCTCCACTGACATCCCTGATTGgtgagtgtacattagagtcctgcc
                                                                   ¦---¦
9021  cttcctcccaccattccatggagatcctgtagtctgtatctttggtcttttatagGTGTATGGTGCAGACTGGCT
                                                              ¦---¦
9101  TCCCTTATAGCAACACAGCTGCCTCCCCAGATCTGTGTGGGAGGAGATGCTGGATAAGTCACCCATCAAATACATCCCT
      ¦---intron 21
9181  CAGgtactcaggtgttcttgtgtgcaccattcctccagagtccgagctcagctcaccacagctccttgcttcca
      ¦---¦
9261  atataccagGTAAAGACACCAGTGTTACTGATGCTGGCCAGGAGACCGACGGGTACCCTTCAAGCAGGGTATGGAGT
                                                                              ¦---intron 22
9341  ATTACCGTGCCCTCAAGGCCCCGAATGTGCCTGTCCGgtgagtgtcacaggggtagtgtcggcagctggtgacaggtaaaac
```

FIG. 4e-1

```
9421   aggcaggacccctccaatgtgcatgtgttgctgctcacatagGCTCCTGCTGTACCCAAGAGCAACCACGCGCTGTCAG
9501   AGGTGGAGGCGGAGTCAGACAGCTTCATGAACGCTGTGCTTTGGCTGCACACACTTGGGCAGTGAAGCCCTATGTTC
9581   TTCTTGAGCTGGGCAGCCCGTCTTGCACTTTGCTCTTGGTAAGCTCCCAGGATCTGACCGAACAGCCAAACAGTCCCTAG
9661   GCTGTGGACTCAGTGAATGGGCAGAGGACTAAGAACTATGTTATCATAATAAAGCGAGACACAGagcctggttttgctg
9741   gttgtaccagcatcccaaccccagtcttgggtttactatccacagtggattcatctctgtcacctgacagagagaa
9821   gccatgagagactcaaccctgcctgtcctgcaaatgggactggtgcagagcaacacagctcttcgctctggtcca
9901   tgtgctgaaacttctacactatccttgcattcccaggcacctctggagatggcggcaccctgccatccatttgaagt
9981   tgttccgggatcagaacacctagagtgtgtgctggtctcttgtaaggagtcaaactcatt
10061  ctctagaaacagagacgaagaagcactctctacagacatagagaaaagtttgctttagtttgataagcagcttgtcatc
10141  tctaagagatcgaaagcggaggcccctactccagctgcacgacccttgttaatccagtccacaaacacagacacgtgaaga
10221  tagctggccagcgcgaggccgtgcaccctggtaagcaagtagtagttccagttcccgaaccttgaccttggcaatgactgaccacctcc
10301  ggcaagtgggccccccgttgcccccttggtaagcaagtcacccagtcaggtagaagaactggtgaaggcttgaccttggcaatgactgaccacctccc
10381  ctgacatcctgccccttggtaagcaagtcacccctagccaccccagtcagccagctccaccacttcccagccagccggcccagcggctctccca
10461  ctgacctcacaagcgcccgtaggggccagccgagttcctttctactcgtctccggtacttcac
10541  attacattcctgactggagatgacctttcatttggccacatgaaggactgctattgcttgtacctggagtgcagacag
10621  gagagg
```

FIG. 4f

```
             10         20         30         40         50         60
acyl-ala-r   MERQVLLSEPQEAAALYRGLSRQPSLSAACLGPEVTTQYGGLYRTVHTEWTQRDLERMEN 70         80         90        100        110        120
acyl-ala-r   IRFCRQYLVFHDGDSVVFAGPAGNSVETRGELLSRESPSGTMKAVLRKAGGTVSGEEKQF
                                                     ||||||||||| ,||||||
HUMDNFA                                              MKAVLRKAGGTDPGEEKQF
                                                              10

130        140        150        160        170        180
acyl-ala-r  LEVWEKNRKLKSFNLSALEKHGPVYEDDCFGCLSWSHSETHLLYVAEKKRPKAESFFQTK
            ||||||||||||||||||||||||||||||||||||||||||||||||||||||||||||
HUMDNFA     LEVWEKNRKLKSFNLSALEKHGPVYEDDCFGCLSWSHSETHLLYVAEKKRPKAESFFQTK
             20         30         40         50         60         70

190        200        210        220        230
acyl-ala-r  ALDISASDDEMARPKKPDQAIKGDQFVFYEDWGETMVSKSIPV-LCVLDIDSGNISVLEG
            |||,||||||,|| ||,,,, ,|  , | ,, | ,||||||||  | ,,  ,,,,, | |
HUMDNFA     ALDVSASDDEIARLKKQTKPSRGISLCFMKT-GRNMVSKSIPVSACWMSRVETSLC-LRG
             80         90        100        110        120        130

240        250        260        270        280        290
acyl-ala-r  VPENVSPGQAFWAPGDTGVVFVGWWHE-PFRICIRYCTNRRSALYYVDLSGGKCELLSDG
            , ,,,| , ,,,| , ,,|, , | , , ,,,,,X|,,|||||||||||| |||||||||,
HUMDNFA     -SLRMCPLDRHFGPLEM-LVWCLWAGGMSLPVGIRFCTNRRSALYYVDLIGGKCELLSDD
             140        150        160        170        180        190
```

FIG. 6A

```
              300       310       320       330       340       350
acyl-ala-r  SIAICSPRLSPDQCRIVYLQYPCLAPHHQCSQLCLYDWYTKVTSVVVDTVPRQLGESFSG
            III,,IIIIIIIIIIIIIIIII,I IIIIIIIIIIIIIIIIIIIII,IIIIIII,III
HUMDNFA     SLAVSSPRLSPDQCRIVYLQYPSLIPHHQCSQLCLYDWYTKVTSVVVDVVPRQIGENFSG
              200       210       220       230       240       250

360       370       380       390       400       410
acyl-ala-r  IYCSLLPLGCWSADSQRVVFDSAQRSRQDLFAVDTQTGSITSLTAAGSAGSWKLLTIDKD
            IIIIIIIIIIIIIIIIIIIIIIIII,IIIIIIIII,I,,IIIII,II,IIIIIIIII,I
HUMDNFA     IYCSLLPLGCWSADSQRVVFDSAQRTRQDLFAVDTQVGTVTSLTAGGSGGSWKLLTIDQD
              260       270       280       290       300       310

420       430       440       450       460       470
acyl-ala-r  LMVAQFSTPSLPPSLKVGFLPPPGKEQSVSWVSLEEAEPIPGIHWGVRVLHPPPDQENVQ
            IIIIIIIIIIIII,IIIIIII,,IIIIIII  IIX     ,,I,,I,   .    .I,..
HUMDNFA     LMVAQFSTPSLPPTLKVGFLPSAGKEQSVLWVSWRRPSPFPTSTGASGCYSHPQSKRMCS
              320       330       340       350       360       370

480       490       500       510       520       530
acyl-ala-r  YADLDFEAILLQPSNPPDKTQVPMYVMPHGGPHSSFVTAWMLFPAMLCKMGFAVLLVNYR
            .I....    II  .  ...I    I  ,I,IIIIIIIIIIIIIIIIIIIIIIIIIIII
HUMDNFA     MLALTLKQSCCSLAALQIRPKCPWWSCP-TGAHSSFVTAWMLFPAMLCKMGFAVLLVNYR
              380       390       400       410       420       430
```

FIG. 6B

```
           540       550       560       570       580       590
acyl-ala-r GSTGFGQDSILSLPGNVGHQDVKDVQFAVEQVLQEEHFDARRVALMGGSHGGFLSCHLIG
           ||||||||||||||||||||||||||||||||||||||||||||,,|| ||||||||,||||||

600       610       620       630       640       650
acyl-ala-r QYPETYSACIARNPVINIASMMGSTDI---PDWCMVETGFPYSNSCLPDLNVWEEMLDKSP
           ||||||,||, ,, , |||,||||| ,| ,, ,,|,,|||||,||,|||||||
HUMDNFA    QYPETYRACL--RTRDHNASMLGSTDILTGAWWRL----ASFSSDCLPDLSVWAEMLDKSP
            500       510       520       530       540

660       670       680       690       700       710
acyl-ala-r IKYIPQVKTPVLLMLGQEDRRVPFKQGMEYYRALKARNVPVRLLLYPKSNHALSEVEAES
           |,| , ,|,| ,|||| , ,,, | ,,, , ,||||||||,|||||||,||
HUMDNFA    IRYSSGEDTTV-TDVGQED---AVCLSRHEYTSSRP-ECAVRLLLYPKSTHALSEVEVES
            550       560       570       580       590       600

720       730
acyl-ala-r DSFMNAVLVLHTHLGS
            ,|
HUMDNFA    AS
```

FIG. 6C

ACYL-PEPTIDE HYDROLASE AND METHODS OF PRODUCTION AND USE

CROSS REFERENCE TO RELATED APPLICATIONS

This application is a division of application Ser. No. 07/429,935, filed Nov. 1, 1989 now U.S. Pat. No. 5,268,267, which is a continuation-in-part of U.S. application Ser. No. 07/296,996, filed Jan. 13, 1989 ABN, which is a continuation-in-part of U.S. application Ser. No. 07/087,936, filed Aug. 21, 1987 ABN, such applications being herein incorporated by reference.

FIELD OF THE INVENTION

The present invention is directed toward the production of Acyl-Peptide Hydrolase by recombinant DNA technology. It is also directed to the use of the enzyme to catalyze hydrolysis of an acylated peptide or protein, and the reaction between a derivatized $N^\alpha$-acetyl amino acid donor and an acceptor protein with a free $\alpha$-$NH_2$ group. The invention further concerns a gene sequence which encodes the rat acyl-peptide hydrolase. The invention is also directed toward the diagnosis of small cell carcinoma through the use of acyl-peptide hydrolase and gene sequences which encode acyl-peptide hydrolase.

BRIEF DESCRIPTION OF THE BACKGROUND ART

Since the discovery of an acetyl group at the amino-terminus of tobacco mosaic virus coat protein, a number of $N^\alpha$-acetylated proteins have been found in animals, plants, and their viruses, and also in bacteria and fungi. $N^\alpha$-acetylation is therefore considered one of the typical modifications of proteins in living organisms. Moreover, in some eukaryotic cells, it has been suggested that more than 80% of the intracellular soluble proteins are $N^\alpha$-acetylated (Brown, J. L., *J. Biol. Chem.* 254:1447–1449 (1979)).

The biological significance of $N^\alpha$-acetylation of proteins is still an open question (see Tsunasawa et al., *Method Enzymol.* 106:165– 170 (1984)). It has been proposed that this post-translational modification protects intracellular proteins from proteolysis. However, this does not hold true for all proteins. In the case of actin from slime mold, proteolytic degradation becomes slower when the protein is $N^\alpha$-acetylated. In contrast, cat hemoglobin is degraded at the same rate irrespective of $N^\alpha$-acetylation (Tsunasawa et al., 1984).

Recent results from DNA sequencing have shown that in structural genes for the secretory proteins that are $N^\alpha$-acetylated, the codon for the acetylated amino-terminal residue is directly preceded by the initiation codon without the insertion of additional codons for amino acids (Tsunasawa et al., 1984). Little effort has been made to understand the relationship between $N^\alpha$-acetylation and the transport of secretory proteins across biological membranes. To understand completely the function of $N^\alpha$-acetylation, it will be important to identify the $N^\alpha$-acetylated amino acids in proteins and peptides on a microanalytical scale. For this purpose, removal of the $N^\alpha$-acetyl group or the $N^\alpha$-acetyl amino acid must be efficiently achieved.

Acyl-Peptide Hydrolase (APH) has been successfully used for the hydrolysis of $N^\alpha$-acylated peptides. One such enzyme, which was purified from animal liver, can liberate the $N^\alpha$-acetyl amino acid from rather short peptides derived from $N^\alpha$-acetylated proteins (Tsunasawa et al., 1984). The substrate specificity is broad for the amino terminal residue. APH cleaves the $N^\alpha$-terminal acetylated or formylated amino acid from a blocked peptide (Jones et al., *BBRC* 126:933 (1985)). This enzyme catalyzes the hydrolysis of a diverse number of peptides and displays different pH optima for certain substrates in doing so. This enzyme may also play a pivotal role in the processing of polypeptide chains during biosynthesis. APH has been purified from rat liver (Tsunasawa et al., *J. Biochem.* 77:89–102 (1975)); [from bovine liver (Gade et al., *Biochim. Biophys. Acta* 662:86–93 (1981))]; from porcine liver (Tsunasawa et al., *J. Biochem.* 93:1217–1220 (1983)); from rat brain (Marks et al., *J. Neurochem.* 41:201–208 (1983)); and from human erythrocytes (Jones et al., *Biochem. and Biophys. Res. Comm.* 126:933–940 (1985)).

A rat liver acyl-peptide hydrolase (APH), which catalyzes the hydrolysis of the acetylated residue from $N^\alpha$-acetylated peptides was recently purified to homogeneity, and various inhibition experiments indicated that it was likely a serine protease, utilizing a charge relay system involving serine, histidine, and probably a carboxyl group (Kobayashi, K. and Smith, J. A., *J. Biol. Chem.* 262:11435–11445 (1987)). However, it is not yet clear whether acyl-peptide hydrolase is a unique serine protease.

In order to facilitate a more complete understanding of the regulation of rat acyl-peptide hydrolase in vivo, it is, therefore, desirable to clone and sequence the rat acyl-peptide hydrolase gene.

SUMMARY OF THE INVENTION

Acyl-peptide hydrolase catalyzes the hydrolysis of an $N^\alpha$-acetylated amino acid residue from an $N^\alpha$-acetylated peptide. Two overlapping, degenerate oligonucleotide probes based on the sequence of a tryptic peptide, derived from purified rat acyl-peptide hydrolase, were synthesized and used to screen a rat liver λgt11 cDNA library. A 2.5 kb cDNA was cloned and sequenced. This clone contained 2364 bp of rat acyl-peptide hydrolase sequence but lacked an initiation codon. Using a 220 bp probe derived from the 5'-end of this nearly full-length cDNA to rescreen the library, full-length clones were isolated, which contained an in-frame ATG codon at nucleotides 6–8 and encoded the $NH_2$-terminal sequence, Met-Glu-Arg-Gln . . . . The DNA sequence encoded a protein of 732 amino acid residues, 40% of which is confirmed by protein sequence data from 19 CNBr or tryptic peptides. The isolated enzyme is $NH_2$-terminally blocked (Kobayashi, K., and Smith, J. A. (1987) *J. Biol. Chem.* 262:11435–11445), and based on the $NH_2$ terminal protein sequence deduced from the DNA sequence and the sequence of the most $NH_2$-terminal CNBr peptide, it is likely that the $NH_2$-terminal residue is an acetylated methionine residue, since such residues are frequently juxtaposed to glutamyl residues (Persson, B., et al., (1985) *Eur. J. Biochem.* 152, 523–527). The RNA blot analysis revealed a single message of 2.7 kb in various rat tissues examined. Although this enzyme is known to be inhibited by diisopropyl fluorophosphate and acetylalanine chloromethyl ketone (Kobayashi, K., and Smith, J. A. (1987) *J. Biol. Chem.* 262:11435–11445), no strong similarity in protein sequence has been found with other serine proteases. This result suggests that acyl-peptide hydrolase may be a unique serene protease.

This invention is directed to a protein Acyl-Peptide Hydrolase (APH), which comprises the amino acid sequence of FIG. 1. It is also directed to the production of APH by recombinant DNA technology, and to the utilization of APH in the hydrolysis or amino-acylation of peptides or proteins. The invention concerns the cloning and sequence analysis of an acyl-peptide hydrolase from rat liver described by Kobayashi, K. et al. (*J. Biol. Chem.* 264:8892–8899 (May, 1989)), which reference is incorporated herein by reference.

A recombinant DNA molecule coding for APH of the present invention may be used to transform any of a number of hosts, creating new sources and unlimited supplies of APH. The invention thus further comprises the genetic sequences coding for an enzyme having the amino acid sequence designated in FIG. 1, vehicles containing the genetic sequence, hosts transformed therewith, enzyme production by transformed host expression, and utilization of the enzyme in hydrolysis or in amino-acylation of peptides or proteins. It is a purpose of this invention to provide new sources of substantially pure APH which would be available in unlimited supply.

Additionally, this invention encompasses the use of the enzyme to catalyze the hydrolysis of an $N^\alpha$-acylated protein, or the reaction between an $N^\alpha$-acetyl amino acid donor and an acceptor protein with a free $\alpha$-$NH_2$ group.

Therefore, additional purposes of this invention are to provide a means of hydrolysis of $N^\alpha$-acylated proteins, and of amino-acylating any polypeptide or protein from an $N^\alpha$-acetyl amino acid donor and an acceptor with a free $\alpha$-$NH_2$ group, by the use of APH.

In detail, the invention concerns Acyl-Peptide Hydrolase in substantially pure form. The invention also concerns Acyl-Peptide Hydrolase free of native glycosylation.

The invention further concerns a recombinant nucleic acid molecule, either RNA, genomic DNA, or cDNA, which contains a genetic sequence coding for Acyl-Peptide Hydrolase. The nucleic acid molecule may be a vector or plasmid.

The invention also concerns a host, such as a bacterium, a yeast, or a mammalian cell, etc., transformed with any of the above-described recombinant nucleic acid molecules.

The invention also concerns a method of producing Acyl-Peptide Hydrolase which comprises:
  (a) providing any of the above-described nucleic acid molecules, wherein the molecule is DNA;
  (b) inserting the DNA molecule into a vector;
  (c) transforming a host system with the vector;
  (d) expressing the Acyl-Peptide Hydrolase DNA sequence of the recombinant DNA molecule in the host; and
  (e) recovering the Acyl-Peptide Hydrolase produced by the expression.

The invention also includes the Acyl-Peptide Hydrolase produced by the above-described method.

The invention also includes the above-described Acyl-Peptide Hydrolase in immobilized form.

The invention also includes a method of hydrolyzing the N-terminal acyl amino acid of an acylated polypeptide, which comprises contacting the polypeptide with the above-described Acyl-Peptide Hydrolase.

The invention also includes a method of catalyzing the reaction between a derivatized $N^\alpha$-acetyl amino acid donor and an acceptor with a free $\alpha$-$NH_2$ which comprises contacting the donor with the acceptor in the presence of the above-described Acyl-Peptide Hydrolase.

The invention also pertains to a method of detecting small cell carcinoma which comprises:
  a. incubating a nucleic acid sample from a patient suspected of having small cell carcinoma, in the presence of a nucleic acid molecule having a sequence selected from the group consisting of:
    a. a sequence which encodes all or part of an acyl-peptide hydrolase enzyme; and
    b. a sequence which is complementary to a sequence which encodes all or part of an acyl-peptide hydrolase enzyme;
  the incubation being under conditions sufficient to permit nucleic acid hybridization to occur between the nucleic acid sample and the nucleic acid molecule, and to thereby form a hybridized molecule; and
  b. detecting, such as by an analysis of restriction fragment length polymorphisms, small cell carcinoma by determining whether the hybridized molecule differs in sequence from a reference molecule, the reference molecule comprising a nucleic acid sample from a normal individual hybridized to a nucleic acid molecule which encodes all or part of an acyl-peptide hydrolase enzyme.

The invention further includes a two stranded nucleic acid molecule comprising:
  A. a first strand having a sequence selected from the group consisting of:
    a. a sequence which encodes all or part of an acyl-peptide hydrolase enzyme; and
    b. a sequence which is complementary to a sequence which encodes all or part of an acyl-peptide hydrolase enzyme; the first strand being hybridized to:
  B. a second strand, the second strand having a sequence which is substantially complementary in sequence to the sequence of the first strand, the complementary sequence of the second strand being derived from an individual suspected of having small cell carcinoma.

DESCRIPTION OF THE FIGURES

FIG. 1 illustrates the amino acid sequence of APH. The protein sequence deduced from the cDNA sequence (FIG. 3) is indicated by the one letter code for the amino acids. The bracket lines indicate the termini of the CB, CB-R, and CB/R peptides. The arrows pointing right indicate that the corresponding amino acid residue was identified as the Pth-amino acid residue during automated Edman degradation (Table 3). A blank indicates that a Pth amino acid was not identified in this degradative cycle. An asterisk indicates that a Pth-Trp together with an unidentified late-eluting Pth-derivative was identified instead of Pth-Lys during this degradative cycle. Cysteine residues were identified as Pth-derivatives of [$^{14}$C] S-carboxymethylcysteine. The active serine is shown at positions 620–627 of FIG. 1 (diagonal-line filled box). The identification of peptides shown here is defined in Table 3.

FIG. 3 shows the nucleotide sequence and deduced amino acid sequence of rat liver acyl-peptide hydrolase. The complete cDNA encoding rat liver acyl-peptide hydrolase was derived by combining the DNA sequence data from APH36.1 and APH2.7 (FIG. 2B). The deduced protein sequence is indicated by the one-letter code for the amino acids.

FIGS. 4A and 4A–4E show the nucleotide sequence of the rat acyl-peptide hydrolase gene and its flanking region. The transcriptional initiation site of the gene is indicated by vertical arrow. The nucleotide at this position is assigned at number 1. The intronic DNA sequence is shown in lower-case letters and the exonic DNA sequence is shown in uppercase letters. The beginning and end of each intron are marked by vertical lines. The translational initiation site is located at nucleotides 625–627. The polyadenylation signal is located at nucleotides 9708–9713. The "TATA" box-like sequence (nucleotides −24 to −30) and the "CAAT box"-like sequence (nucleotides −95 to −99) are boxed. The GC repeats are underlined. Tandem 200 bp repeats are indicated by a dashed underline.

FIG. 5A shows overlapping λ recombinant phages containing the acyl-peptide hydrolase gene. The overlapping genomic clones, APHE5 and APHH6, together containing the entire acyl-peptide hydrolase gene, are indicated by solid horizontal lines. FIG. 5B shows the restriction map of the acyl-peptide hydrolase gene and its flanking regions. The EcoRI (E), BamHI (B), HindIII (H), and PstI (P) sites are indicated by vertical bars. The 5' (left) to 3' (right) transcriptional orientation of this gene is shown. FIG. 5C shows the exon-intron organization of rat acyl-peptide hydrolase gene. The location of the 23 exons within the rat acyl-peptide hydrolase gene are indicated by filled boxes. The locations of the translational initiation codon, ATG, and the polyadenylation signal, AATAAA, are marked by vertical lines.

FIG. 6 shows a comparison of the amino acid sequences of acyl-peptide hydrolase and the DNF 15S2 protein.

Figures 2A, 2B:
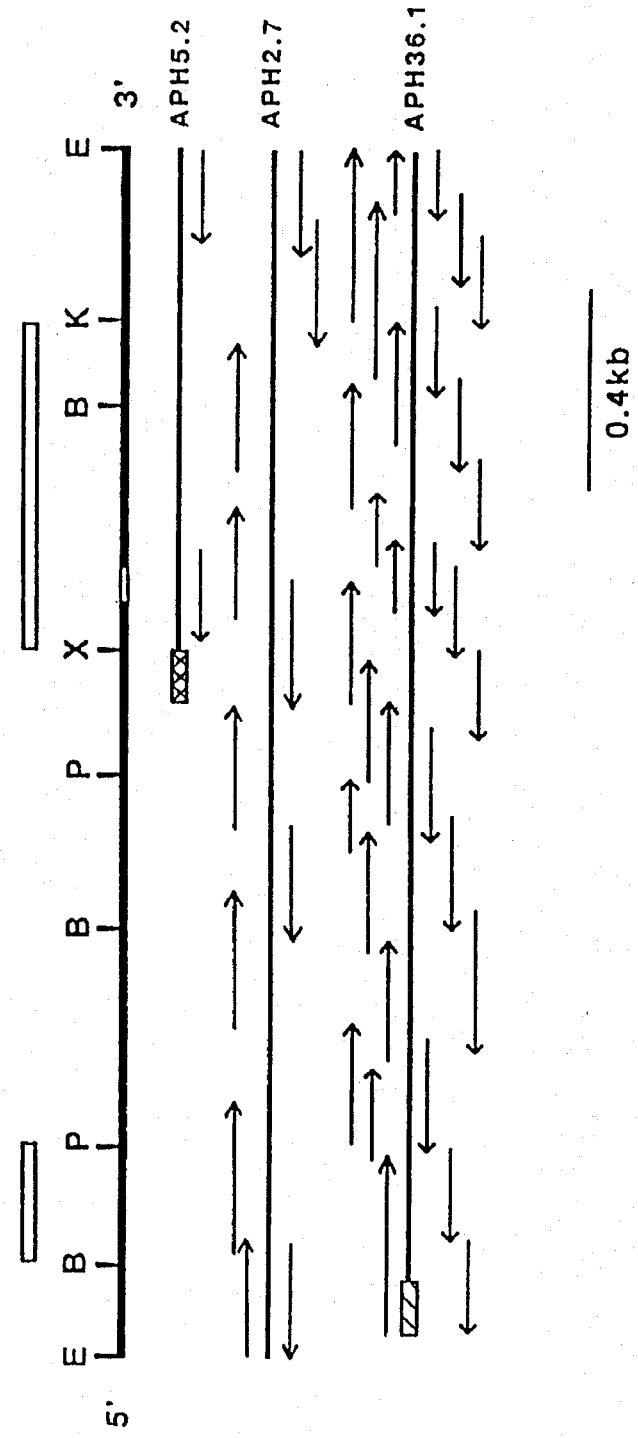
FIGS. 2A and B illustrate the cloning and sequencing of the cDNA encoding rat acyl-peptide hydrolase. (A) Oligonucleotide probes used for the initial screening of the rat liver λgt11 cDNA library. The amino acid sequence of an RPLC-purified tryptic peptide (CB18-R11-13-c; Table 3) was used as the basis for the synthesis of two overlapping degenerate oligonucleotides, YS17.2 and YS20.1. (B) Restriction map and DNA sequencing strategy of the clones. Using the degenerate oligonucleotides in FIG. 2A, APH5.2 was obtained from a rat liver λgt11 cDNA library, as described below. The arrows indicate the direction and extent of DNA sequence determination for each fragment. DNA sequence analysis for this clone revealed the expected hybridization site near its 5' end (open region in bold line), a poly(A) sequence at its 3' end, and an unrelated sequence at its 3' end (cross-hatched box). After rescreening the rat liver λgt11 cDNA library with the XmnI-KpnI fragment derived from APH5.2 (longer open box), APH36.1 lacked an ATG initiation codon and also contained a 120 base pair fragment encoding rat serum albumin (box with diagonals). After rescreening the library with a 220 bp BanII-PstI fragment derived from APH36.1 (shorter open box), APH2.7 was cloned, which was subsequently subcloned into Bluescript plasmid (Stratagene) and sequenced in part. Abbreviations: B, BanI; P, PstI; X, XmnI; and K, KpnI.

In the Figures, the amino acids have been designated by single letters of the alphabet such that: A=Alanine, B=Aspartic Acid or Asparagine, C=Cysteine, D=Aspartic Acid, E=Glutamic Acid, F= Phenylalanine, G=Glycine, H=Histidine, I=Isoleucine, K=Lysine, L=Leucine, M=Methionine, N=Asparagine, P=Proline, Q=Glutamine, R=Arginine, S=Serine, T=Threonine, V=Valine, W= Tryptophan, Y=Tyrosine, Z=Glutamine or Glutamic Acid.

DETAILED DISCUSSION OF THE INVENTION

Definitions

To aid in the understanding of the specification and claims, including the scope to be given such terms, the following definitions are provided.

Transcription
The process of producing mRNA from a structural gene.

Translation
The process of producing a polypeptide from mRNA.

Expression
The process undergone by a structural gene to produce a polypeptide. It is a combination of transcription and translation.

Plasmid
A circular double-stranded DNA molecule that is not a part of the main chromosome of an organism containing genes that convey resistance to specific antibiotics. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant."

Cloning Vehicle
A plasmid, phage DNA or other DNA sequences which are able to replicate in a host cell. The cloning vehicle is characterized by one or a small number of endonuclease recognition sites at which such DNA sequences may be cut in a determinable fashion without loss of an essential biological function of the DNA, which may contain a marker suitable for use in the identification of transformed cells. Markers, for example, are tetracycline resistance or ampicillin resistance. A cloning vehicle is often called a vector.

Recombinant DNA Molecules or Hybrid DNA
A molecule consisting of segments of DNA from different genomes which have been joined end-to-end outside of living cells and have the capacity to infect some host cell and be maintained therein.

Operator
A DNA sequence capable of interacting with the specific repressor, thereby controlling the transcription of adjacent gene(s).

Promoter
A DNA sequence in which RNA polymerase binds and initiates transcription of an adjacent gene(s).

Acyl-Peptide Hydrolase (APH)
This term is meant to include an acyl-peptide hydrolase(s) from any species, which has the activity of releasing the $N^\alpha$-terminal acylated amino acid from any protein or peptide in an in vivo or in vitro system. The term acyl-peptide hydrolase is also used in this invention to include any analogue, homologue, mutant or derivative of a naturally occurring acyl-peptide hydrolase, which cleaves the $N^\alpha$-acetylated amino acid from the $N^\alpha$-terminal portion of a peptide or a protein. The term is also meant to include fragments having less than the naturally-occurring number of amino acids, such as partial fragments of natural acyl-peptide hydrolases which retain the activity of cleaving the acylated amino acid from the N-terminal end of a protein or peptide. The term is also used to include any product which comprises the sequence of a naturally occurring acyl-peptide hydrolase or analogue thereof, together with one or more flanking amino acids, which show acyl-peptide hydrolase activity. The term acyl-peptide hydrolase also includes synonyms such as acyl-amino acid releasing factor, acyl-amino acid releasing enzyme, acyl-amino peptide hydrolase and acetylaminoacyl-p-nitroanilidase.

Substantially Pure Form
As used herein, the term "substantially pure" or "substantially purified" is meant to describe the protein which is substantially free of any compound normally associated with the factor in its natural state. The term is further meant to describe the factor which is homogeneous by one or more purity or homogeneity characteristics used by those of ordinary skill in the art. For example, a substantially pure factor will show constant and reproducible characteristics within standard experimental deviations for parameters such as the following: molecular weight, chromatographic techniques and such other parameters. The term, however, is not meant to exclude artificial or synthetic mixtures of the factor with other compounds. The term is also not meant-to exclude the presence of minor impurities which do not interfere with the biological activity of the factor, and which may be present, for example, due to incomplete purification.

The molecular weight of rat liver APH, as estimated by gel filtration, is 290,000–320,000. There appear to be four identical subunits, with one active serine per subunit. The $N^\alpha$-terminus of the APH is acylated. APH appears to be a serine protease, with a charge relay system involving serine, histidine and carboxyl groups. The active serine is shown at positions 620–627 of FIG. 1 (diagonal-line filled box). The amino acid sequence of this site is MGGSHGGF. The environment of the active site differs from other proteases of the trypsin family, due to the presence of histidine, and the lack of aspartic acid. Although APH displays broad specificity for substrates, it cleaves Ac-Ala-, Ac-Ser-, and Ac-Met- containing peptides (the most common N-terminal acetylated residues) more effectively than other acylated dipeptides. APH has very low or no activity toward Ac-Trp-, Ac-Asp-, Ac-Glu, Ac-Arg-, Ac-Phe, and Ac-Pro- containing peptides.

Acyl-Peptide Hydrolase (APH) should be distinguished from $N^\alpha$-acetyltransferase, which catalyzes the reaction in which a protein accepts the acetyl group from an acetyl-CoA (Tsunasawa et al., *Methods in Embryology* 106:165–170 (1984)). Acyl-Peptide Hydrolase should also be distinguished from Aminoacylase (Szajani, *Acta Biochim. et Biophys. Acad. Sci. Hung.* 15:223–228 (1980)) [also known as α-N-Acylamino acid hydrolase (Gade et al., *Biochim. Biophys. Acta* 662:86–93 (1981))].

Although APH has been isolated and purified from several sources, there has been no sequencing to date of APH. The present invention discloses that sequence (FIG. 1).

The DNA sequence coding for APH may be derived from a variety of sources. For example, mRNA encoded for APH may be isolated from the tissues of any species that produces APH, by using the Northern blot method (Alwine et al., *Method Enzymol.* 68:220–242 (1979)), and labeled oligonucleotide probes. The mRNA may then be converted to cDNA by techniques known to those skilled in the art. The probes may be synthesized based on the known amino acid sequence of APH peptides.

Alternately, degenerative DNA probes may be used to screen a DNA library of a species that produces APH, thereby isolating a clone that contains the DNA sequence encoding APH. The DNA library is created by the fragmentation, using one or more restriction endonucleases of the genomic DNA, followed by incorporation into vectors, and use thereof to transform host cells, which are then plated and screened.

The DNA probe may be labeled with a detectable group. Such detectable group can be any material having a detectable physical or chemical property. Such materials have been well-developed in the field of immunoassays and in general most any label useful in such methods can be applied to the present invention. Particularly useful are enzymatically active groups, such as enzymes (see *Clin. Chem.* 22:1243 (1976)), enzyme substrates (see British Pat. Spec. 1,548,741), coenzymes (see U.S. Pat. Nos. 4,230,797 and 4,238,565) and enzyme inhibitors (see U.S. Pat. No. 4,134, 792); fluorescers (see *Clin. Chem.* 25:353 (1979)); chromophores; luminescers such as chemiluminescers and bioluminescers (see *Clin. Chem.* 25:512 (1979)); specifically bindable ligands; proximal interacting pairs; and radioisotopes such as $^3$H, $^{35}$S, $^{32}$P, $^{125}$I and $^{14}$C. Such labels and labeling pairs are detected on the basis of their own physical properties (e.g., fluorescers, chromophores and radioisotopes) or their reactive or binding properties (e.g., enzymes, substrates, coenzymes and inhibitors). For example, a cofactor-labeled probe can be detected by adding the enzyme for which the label is a cofactor and a substrate for the enzyme. For example, one can use an enzyme which acts upon a substrate to generate a product with a measurable physical property. Examples of the latter include, but are not limited to β-galactosidase, alkaline phosphatase and peroxidase.

A DNA sequence encoding APH may be recombined with vector DNA in accordance with conventional techniques, including blunt-ended or stagger-ended termini for ligation, restriction enzyme digestion to provide appropriate termini, filling in of cohesive ends as appropriate, alkaline phosphatase treatment to avoid undesirable joining, and ligation with appropriate ligases.

To express APH, transcriptional and translational signals recognized by an appropriate host element are necessary. Eukaryotic hosts may be mammalian cells capable of culture in vitro, particularly leukocytes, more particularly myeloma cells or other transformed or oncogenic lymphocytes, e.g., EBV-transformed cells. Alternatively, non-mammalian cells may be employed, such as bacteria, fungi, e.g., yeast, filamentous fungi, or the like.

Possible hosts for APH production are mammalian cells, grown in vitro in tissue culture or in vivo in animals. Mammalian cells may provide post-translational modifications to APH molecules including correct folding or glycosylation of the correct sites. Mammalian cells which may be useful as hosts include cells of fibroblast origin such as VERO or CHO-K1, or cells of lymphoid origin, such as the hybridoma SP2/O-AG14 or the myeloma P3x63Sgh, and their derivatives. Usually the APH construct will be part of a vector having a replication system recognized by the host cell:

In a preferred embodiment, a prokaryotic cell is transformed by a plasmid carrying the APH encoded gene. Bacterial hosts of particular interest include *E. coli* K12 strain 294 (ATCC 31446), *E. coli* X1776 (ATCC 31537), *E. coli* W3110 (F$^-$, lambda$^-$, prototrophic (ATCC 27325)), and other enterobacteriacaes such as *Salmonella typhimurium* or *Serratia marcescens*, and various Pseudomonas species. Under such conditions, the APH will not be glycosylated. The prokaryotic host must be compatible with the replicon and control sequences in the expression plasmid. A prokaryotic host with a plasmid containing the cDNA encoded for APH has been deposited on Aug. 21, 1987 at the American Type Culture Collection, Rockville, Md., USA, and given accession number ATCC 67504.

In general, such vectors containing replicon and control sequences which are derived from species compatible with a host cell, are used in connection with the host. The vector ordinarily carries a replicon site, as well as specific genes which are capable of providing phenotypic selection in transformed cells. The expression of the APH encoded DNA can also be placed under control of other regulatory sequences which may be homologous to the organism in its untransformed state. For example, lactose-dependent *E. coli* chromosomal DNA comprises a lactose or lac operon which mediates lactose utilization by elaborating the enzyme β-galactosidase. The lac control elements may be obtained from bacteriophage lambda plac5, which is infective for *E. coli*. The lac promoter-operator system can be induced by IPTG.

Other promoter/operator systems or portions thereof can be employed as well. For example, colicin E1, galactose, alkaline phosphatase, tryptophan, xylose, tax, and the like can be used.

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, H., *Mol. Cel. Biol.* 3:280 (1983), and others.

A wide variety of transcriptional and translational regulatory sequences may be employed, depending on the nature of the host. The transcriptional and translational signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation signals may also be selected which allow for repression or activation, so that expression of the genes may be modulated. Of interest are regulatory signals which are temperature-sensitive so that varying the temperature, expression can be repressed or initiated, or are subject to chemical regulation, e.g., metabolite.

Once the vector or DNA sequence containing the constructs has been prepared for expression, the DNA constructs may be introduced to an appropriate host. Various techniques may be employed, such as protoplast fusion, calcium phosphate precipitation, electroporation or other conventional techniques. After the fusion, the cells are grown in media and screened for appropriate activities. Expression of the gene(s) results in production of the APH.

The host cells for APH production may be immortalized cells, primarily myeloma or lymphoma cells. These cells may be grown in an appropriate nutrient medium in culture flasks or injected into a synergistic host, e.g., mouse or rat, or immunodeficient host or host site, e.g., nude mouse or hamster pouch.

The APH of the invention may be isolated and purified in accordance with conventional conditions, such as extraction, precipitation, chromatography, affinity chromatography, electrophoresis, or the like.

Uses

APH, once produced and purified, can be used, for example, in a pharmaceutical manufacturing environment to hydrolyze an $N^\alpha$-acylated peptide, or to amino-acylate the $N^\alpha$-terminus of a peptide. The former is carried out in an aqueous solution, and makes refractory proteins susceptible to Edman sequencing. The latter may be performed in a near anhydrous environment, and is useful in reducing degradation of proteins to be used therapeutically. See the discussion following A. Klibinov, "Unconventional Catalytic Properties of Conventional Enzymes," in *Basic Biology of New Developments in Biotechnology*, pp. 497–518 (A. Hollaender, ed. 1973), on the use of enzymes in biphasic systems for organic synthesis.

The near anhydrous environment will alter the substrate specificity of APH, such that the amino-acylation of peptides takes place. Substrate specificity of an enzyme in organic solvents may be radically different from, and sometimes opposite to, those in water (see Zaks et al., *J. Am. Chem. Soc.* 108:2767–2768 (1986)). It has been shown that peptides can be synthesized by trypsin and α-chymotrypsin in solvents miscible or immiscible with water (see Pugniere et al., *Proteins: Structure, Function, and Genetics* 1:134–138 (1986)). Porcine pancreatic, yeast, and mold lipases have been shown to vigorously act as catalysts in a number of nearly anhydrous solvents. The activity of the lipases in the organic media depends on the pH of the aqueous solution from which the lipase is recovered. The maximum lipase activity in the organic solvent coincides with the pH optimum of the enzymatic activity in water (see Zaks et al., *Proc. Nat'l Acad. Sci. USA* 82:3192–3196 (1985)). It has also been shown that a serine carboxypeptidase, such as carboxypeptidase Y derived from yeast, can synthesize a peptide from the reaction of an amino acid ester or amide or other substrate with an amino acid or other amine component (U.S. Pat. No. 4,339,534).

Enzymes such as APH can vigorously function as catalysts in organic solvents, provided that some basic rules are followed. These rules include: (1) a proper choice of solvent (with hydrophobic ones being the best if they do not strip the essential layer of water from the enzyme molecule); (2) the use of an enzyme recovered from an aqueous solution of the pH optimal for enzymatic activity; and (3) elimination of diffusional limitations by vigorous agitation and fine dispersion of the enzyme powder in the organic solvent (see Zaks et al., 1986).

The reactants in the APH-catalyzed condensation reaction are acceptor polypeptides, e.g., proteins with a free $N^\alpha$-terminal group, and a substrate such as a benzyl alcohol derivative of an acylated amino acid. Concentration of substrate needs to be sufficient to drive the amino-acylation reaction. The solvent chosen is a hydrophobic one that does not strip the essential layer of water molecules surrounding the enzyme. The APH, antecedent to its placement in the solvent, is recovered from an aqueous solution of the pH optimal for enzymatic activity. Dispersion of the fine APH powder in the solvent, and vigorous agitation is used to overcome diffusional limitations (Zaks et al., *J. Am. Chem. Soc.* 108:2767–2768 (1986)). Additionally, the organic environment will facilitate extraction of the APH due to enzyme insolubility in organic media (Zaks et al., *Proc. Nat'l Acad. Sci. USA* 82:3192–3196 (1985)).

APH may be suspended in its fine hydrated powder form, or may be immobilized on a carrier. The stability of enzymes toward inactivating agents, such as the monohydric alcohols is often enhanced by immobilization. It has been shown that trypsin and α-chymotrypsin, when immobilized on an insoluble alumina-phosphocolamine complex, demonstrate remarkable resistance toward organic solvents, including water-miscible monohydric alcohols (Pugniere et al., 1986). APH may be immobilized by methods known to those skilled in the art, on beads and other carriers, which then may be used in batches or columns.

Having now generally described this invention, the same will be better understood by reference to specific examples, which are included herein for purposes of illustration only, and are not intended to be limiting unless otherwise specified.

EXAMPLES

Example 1—Extraction and Purification of Acyl-Peptide Hydrolase (APH)

Materials—DEAE Sepharose CL-6B, FPLC columns (Mono Q HR5/5, and Mono S HR5/5), Sephacryl S-300 superfine, Octyl-Sepharose, and Polybuffer 74 were from Pharmacia. Spherogel CAA-HIC column (0.46×10 cm) was from Beckman. Hydroxylapatite (Biogel HT) was from BioRad. Glycerol was from BRL. Reactigel 6X was from Pierce. Amino acids (Ac-L-Ala) were from Sigma. All other chemicals were reagent grade or better.

Enzyme Purification—APH was purified from 300 g of rat liver (male, CD strain) as described by Tsunasawa et al., *J. Biochem. (Tokyo)* 77:89–102 (1975), except for the substitution of DEAE-Sepharose CL-6B and Sephacryl S-300 for DEAE cellulose and Sepharose 6B, respectively. The column sizes and gradients were also changed. For hydroxylapatite chromatography, the starting gradient was 5 mM phosphate buffer instead of 20 mM phosphate, and 10% glycerol was used in the gradient. Four mg of purified enzyme were obtained. During DEAE-Sepharose CL-6B chromatography, an increase in total activity was observed. In order to confirm the homogeneity of the protein from the Sephacryl S-300, additional chromatography was carried out: (i) ion-exchange chromatography with Pharmacia FPLC system on Mono Q and Mono S with various buffers at pH's between 5 and 8; (ii) hydrophobic interaction chromatography on Octyl-Sepharose and Spherogel CAA-HIC; (iii) chromatofocusing on Mono P with Polybuffer 74; and (iv) affinity chromatography using Ac-L-Ala—Sepharose, prepared from Reacti-Gel 6X (Pierce) and acetyl-L-alanine. In no case was further separation or increased activity observed. The purification is summarized in Table 1.

Example 2—Amino Acid Sequencing of Tryptic and Cyanogen Bromide Fragments of APH Materials—APH was purified as in Example 1. Purity was confirmed by SDS polyacrylamide gel electrophoresis by the method of Laemmli, *Nature* 227:680–685 (1970).

UV measurements were obtained using a Hewlett-Packard 8450A UV Spectrophotometer. The amount of protein was determined by the method of Bradford, M. M. (*Anal. Biochem.* 72:248–254 (1976)) using bovine serum albumin as a standard and expressed in nmol of rat liver acyl-peptide hydrolase subunit, assuming that 1 nmol of enzyme refers to 1 nmol of the $M_r$=80,000 subunit of the enzyme (Kobayashi, K. and Smith, J. A., *J. Biol. Chem.* 262:11435–11445 (1987)). Radioactive samples were counted on a Beckman LS 3801 scintillation counter.

Cyanogen bromide, guanidine-HCl, 2-mercaptoethanol, trifluoroacetic acid (TFA), were obtained from Pierce. Acetonitrile (HPLC grade UV cut-off 188 nm) was from J. T. Baker. Trypsin treated with N-tosyl-PheCh$_2$Cl was purchased from Worthington. Bradford protein assay reagent and electrophoresis reagents were obtained from Bio-Rad, except for molecular weight markers and Tris, which were purchased from Sigma. Zwittergent 3–14 was from Calbiochem and [$^{14}$-C] iodoacetic acid (9.8 mCi/mmol) was from New England Nuclear. All other reagents were the purest grade that was commercially available.

Amino Acid Analysis—The acyl-peptide hydrolase was dialyzed extensively against 0.1M acetic acid, lyophilized, and hydrolyzed at 110° C. for 24 hr and 48 hr in 6M HCl containing 0.1% phenol. The amino acid composition was determined using a Beckman Amino Acid Analyzer (see Moore, S., In: *Chemistry and Biology of Peptides*, (Meinhofer, J., Ed.), pp.629–652, Ann Arbor Science, Ann Arbor, Mich. (1972)) (Table 2).

TABLE 2

Amino Acid Composition of Rat Liver Acyl-peptide Hydrolase
The theoretical composition was determined from the primary sequence deduced from the nucleotide sequence in FIG. 3. The observed composition was estimated by amino acid analysis of the purified rat liver acyl-peptide hydrolase (N = 3). The observed composition was calculated assuming a subunit $M_r$ = 80,000.

| Amino Acid | Theoretical | Observed |
| --- | --- | --- |
| Asx | 57 | 55 |
| Thr | 29 | 29 |
| Ser | 67 | 64 |
| Glx | 80 | 84 |

TABLE 1

Purification of Acyl-peptide Hydrolase from Rat Liver

| Step | | Activity (unit) | Protein (mg) | Specific Activity (unit/mg) | Yield (%) | Purification |
| --- | --- | --- | --- | --- | --- | --- |
| 1 | Homogenate | 194 | 44200 | 0.00439 | 100 | 1.00 |
| 2 | 12000 × g Supernatant | 194 | 39400 | 0.00492 | 100 | 1.12 |
| 3 | Ammonium Sulfate (20–50%) | 150 | 25400 | 0.00591 | 77 | 1.35 |
| 4 | Heat Treatment | 139 | 2520 | 0.0552 | 65 | 11.5 |
| 5 | DEAE-Sepharose | 208 | 29.3 | 7.10 | 108 | 1630 |
| 6 | Hydroxylapatite | 148 | 5.90 | 25.1 | 76 | 5780 |
| 7 | Sephacryl S-300 | 118 | 4.04 | 29.2 | 61 | 6090 |

TABLE 2-continued

Amino Acid Composition of Rat Liver Acyl-peptide Hydrolase
The theoretical composition was determined from the primary sequence deduced from the nucleotide sequence in FIG. 3. The observed composition was estimated by amino acid analysis of the purified rat liver acyl-peptide hydrolase (N = 3). The observed composition was calculated assuming a subunit $M_r$ = 80,000.

| Amino Acid | Theoretical | Observed |
|---|---|---|
| Gly | 54 | 52 |
| Ala | 45 | 45 |
| Val | 61 | 61 |
| Met | 19 | 15 |
| Ile | 24 | 23 |
| Leu | 75 | 77 |
| Tyr | 24 | 26 |
| Phe | 29 | 36 |
| His | 19 | 19 |
| Lys | 30 | 31 |
| Arg | 34 | 34 |
| Pro | 50 | 65 |
| Cys | 19 | ND[a] |
| Trp | 16 | ND |
| TOTAL | 732 | |

[a]Abbreviations: Asx = Asn + Asp; Glx = Gln + Glu; ND, not determined

Reduction of Disulfide Bonds and Alkylation with Iodoacetic Acid—Purified rat APH (3 nmol) was dissolved in 0.5M Tris-HCl (pH 8.5) containing 7M guanidine HCl/2 mM EDTA, and reduced with 8-10 mM 2-mercaptoethanol under argon at a room temperature for 12 hr or at 37° C. for 3 hr. To the mixture (0.19 ml), [$^{14}$C] iodoacetic acid (2.6 μmol in 30 μl 10.5M Tris-HCl (pH 8.5)/7M guanidine HCl/2 mM EDTA) was added and the reaction was carried out for 1 hr at 37° C. in the dark. 2-Mercaptoethanol was then added to a final concentration of 0.2M. The protein was desalted either by precipitating with four volumes of acetone/methanol (3:1 v/v) or by dialysis against 0.1M acetic acid and lyophilized in a Savant concentrator/evaporator.

Cyanogen Bromide Cleavage—The carboxymethylated protein was dissolved in 70% formic acid (0.1–0.2 ml), to which 10–15 μl CNBr solution (100 mg/ml in 70% formic acid) was added. The mixture was incubated at room temperature for 24 hr and vacuum dried after the dilution with water. The CNBr-cleaved peptide fragments were purified by reversed-phase HPLC (RPLC) or by lyophilization in a Savant concentrator/evaporator or further fragmented by tryptic digestion.

Digestion with Trypsin—The crude mixture of CNBr peptides (3 nmol) were dissolved in 0.2 ml of 0.2M ammonium bicarbonate containing 0.2% Zwittergent 3–14 and digested with trypsin (50 pmol) treated with N-tosyl-PheCH$_2$Cl for 20 hr at 37° C. The digest was vacuum dried and dissolved in 6M guanidine HCl in 0.1% TFA for RPLC purification.

Purification of Peptide Fragments by Reversed-Phase HPLC—The peptides were purified by RPLC on a Beckman HPLC system 344, using a C$_4$ column (Vydac, 0.46×25 cm, 10 micron particle with 300 Å pore size) for CNBr fragments or a Phenyl column (Vydac, 0.46×25 cm, 5 micron particle with 300 Å pore size) for tryptic fragments. The crude peptide mixture was applied to the column equilibrated with 0.1% TFA and eluted with 0–80% linear gradient of acetonitrile in 0.1% TFA (for CB-R and CB peptides) or with 0–60% acetonitrile in 0.1% TFA (for CB/R peptides) in 160 min at a flow rate of 1 ml/min. A mixture of tryptic peptides derived from a crude mixture of CNBr peptides was applied as described above, and eluted with a 0–60% linear gradient of acetonitrile in 0.1% TFA in 180 minutes at a flow rate of 1 ml/min. The elutions were monitored both by 214 nm and 280 nm absorbance. Each peak was collected manually, and, if necessary, further purified by isocratic RPLC using the same column after being dried and redissolved in 0.2 ml of 6M guanidine HCl-0.1% TFA. The optimum concentration of acetonitrile for separating the peptides each fraction was estimated from the elution pattern of the first HPLC (see equation of Wong et al., *Proc. Nat'l Acad. Sci. USA* 82:7711–7715 (1985)).

Peptide Sequencing—Peptide sequence analyses were carried out using an Applied Biosystems 470A Protein Sequencer and an Applied Biosystems 120A Pth Analyzer (see Hewick et al., *J. Biol. Chem.* 256:7900–7997 (1981)) (Table 3).

TABLE 3

Protein Sequence Analysis

The CNBr and tryptic peptides were derived and sequenced as described above. The peptides are identified according to cleavage and purification; CB, a CNBr cleavage fragment purified by RPLC; CB-R, an RPLC-purified tryptic peptide derived from an RPLC-purified CNBr peptide; and CB/R, a RPLC-purified tryptic peptide derived from a crude mixture of CNBr peptides. The recovery of Pth-amino acid detected in each degradative cycle is indicated in pmoles from which the repetitive yield is calculated. The numbers correspond to various manually collected fractions derived from gradient RPLC, and the lowercase letters correspond to the various manually collected fractions derived from isocratic RPLC, required for further purification.

| Peptide | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | RY[a] |
|---|---|---|---|---|---|---|---|---|---|---|---|---|---|---|---|---|---|---|---|---|---|---|---|---|---|
| CB17-R13 | Glu 249 | Arg 106 | Gln 258 | Val 299 | Leu 285 | Leu 254 | Ser 139 | Glu 234 | Pro 139 | Gln 119 | Glu 90 | Ala 133 | Ala 140 | ASla 133 | Leu 87 | Tyr 82 | Arg 14 | | | | | | | | 92% |
| CB16-R18, 19,-c | Gly 112 | Leu 21 | Ser 304 | Arg 78 | Gln 152 | Pro 119 | Ser 43 | Leu 93 | Ser 163 | Ala 80 | Ala 76 | Cys 107 | Leu 63 | Gly 107 | Pro 51 | Glu 40 | Val 41 | Thr 54 | Thr 52 | Gln 22 | Tyr 19 | Gly 25 | Gly 24 | Leu 20 | 89% |
| CB17-R3 | Thr 170 | Val 185 | His 117 | Thr 62 | Glu 179 | Trp 37 | Thr 89 | Glu 39 | Arg 8 | | | | | | | | | | | | | | | | 89% |
| CB/R97 | Gln 228 | Tyr 108 | Leu 220 | Val 133 | Phe 121 | His 84 | Asp 57 | Gly 76 | Asp 116 | Ser 186 | Val 67 | Val 90 | Phe 63 | Ala 56 | Gly 60 | Pro 46 | Ala 51 | Gly 53 | Asn 20 | Ser 81 | Val 28 | Glu 11 | Thr 25 | | 93% |
| CB/R96 | Ala 149 | Gly 98 | Gly 90 | Thr 126 | Val 92 | Ser 108 | Gly 108 | Glu 78 | Glu 42 | Trp[b] 52 | Phe 46 | Gln 27 | Leu 25 | Glu 35 | Val 25 | 13 | | | | | | | | | 93% |
| CB17-R33 | Ser 140 | Phe 143 | Asn 9 | Leu 85 | Ser 76 | Ala 54 | Leu 45 | Glu 37 | Lys 35 | | | | | | | | | | | | | | | | 81% |
| CB16-R5 | Ala 535 | Glu 316 | Ser 152 | Phe 293 | Phe 277 | | Thr 172 | Lys 46 | | | | | | | | | | | | | | | | | N/A |
| CB/R109 | Ser 162 | Ala 446 | Leu 455 | Tyr 400 | Tyr 411 | Val 245 | Asp 103 | Leu 285 | Ser 119 | Gly 216 | Gly 153 | Trp 33 | Cys 136 | Glu 92 | Leu 71 | Leu 114 | Ser 78 | Asp 29 | Gly 33 | Ser 45 | Leu 29 | Ala 29 | Ile 22 | | 90% |
| CB/R101 | Ser 471 | Arg 752 | Gln 455 | Asp 909 | Leu 626 | Phe 497 | Ala 558 | Val 441 | Asp 330 | Thr 432 | Thr 212 | Thr 341 | Gly 280 | Ser 242 | Ile 135 | | Ser 170 | Leu 70 | Thr 110 | Ala 81 | Ala 116 | Gly 88 | Ser 83 | | 85% |
| CB18-R15 | Val mix | Gly 83 | Phe 35 | Leu 34 | Pro 43 | Pro 49 | Pro 49 | Gly 26 | Trp 18 | Glu 20 | Gln 16 | Ser 16 | Val 10 | Ser 15 | | Val 6 | Ser 7 | Leu 5 | Glu 7 | Glu 11 | Ala 6 | | Pro 6 | | 89% |
| CB18-R11-13-c | Val 57 | Leu 62 | | Pro 120 | Pro 185 | Pro 49 | Asp 59 | Glu 15 | Glu 34 | Asn 13 | Val 51 | Gly 13 | Tyr 62 | Ala 57 | Asp 7 | Leu 11 | | Phe 17 | Gln 3 | Ala 15 | Ile 10 | Leu 4 | Leu 6 | Gln 5 | N/A |
| CB18-R11-13-b | Val 258 | Leu 138 | | Pro 104 | Pro 112 | | | | | | | | | | | | | | | | | | | | |
| CB19-R9 | Val 131 | Ser 28 | Thr 35 | Gly 93 | Phe 37 | Gly 30 | Gln 18 | Asp 58 | Ser 18 | Ile 14 | Leu 14 | Ser 10 | Leu 10 | Pro 12 | Gly 17 | Asn 11 | Val 10 | Gly 16 | His 6 | Gln 5 | | Val 5 | | | 92% |
| CB/R16, 17,-o | Val 190 | Glu 42 | Thr 100 | Gly 63 | Phe 53 | Pro 62 | Tyr 46 | Ser 44 | Asn 25 | Ser 46 | Cys 21 | Leu 23 | Pro 18 | Asp 7 | | Asn 9 | Val 9 | Leu 70 | Thr 110 | Ala 81 | Leu 29 | Ala 29 | Ser 83 | | 88% |
| CB/R80 | Leu 606 | Asp 361 | Lys 641 | Ser 600 | Pro 493 | Ile 365 | Lys 373 | Tyr 348 | Ile 254 | Pro 311 | Val 208 | Val 191 | Lys 115 | | | | | | | | | | | | 88% |
| CB/14-n | Glu 209 | Tyr 57 | Tyr 50 | Arg 62 | Ala 62 | Leu 27 | Lys 40 | Ala 54 | Arg 30 | Asn 56 | Val 57 | Pro 24 | Val 27 | Arg 17 | Leu 20 | Leu 30 | Leu 28 | Tyr 14 | Pro 10 | Lys 3 | Ile 6 | | | | 92% |
| CB16-R8 | Ser 172 | Asn 119 | His 31 | Ala 90 | Ser 66 | Pro 27 | | Val 57 | Glu 55 | Ala 51 | Gln 54 | Ser 37 | Asp 52 | Ser 54 | Phe 9 | | | | | | | | | | 92% |
| CB12 | Asn 169 | Ala 206 | Val 164 | Leu 91 | Leu 84 | Leu 74 | His 137 | Thr 88 | His 109 | Leu 53 | Gly 63 | Ser 43 | Thr 21 | Gly 29 | Phe 22 | Gly 29 | Gln 15 | | Ser 14 | Ile 9 | Leu 9 | Ser 9 | | | 88% |
| CB19-R12 | Gly 111 | Phe 60 | Ala 61 | Val 58 | Leu 73 | | Val 50 | | Tyr 49 | | Gly 46 | Ser 37 | | | | | | | | | | | Leu 8 | Pro 8 | 89% |

TABLE 3-continued

Protein Sequence Analysis

The CNBr and tryptic peptides were derived and sequenced as described above. The peptides are identified according to cleavage and purification; CB, a CNBr cleavage fragment purified by RPLC; CB-R, an RPLC-purified tryptic peptide derived from an RPLC-purified CNBr peptide; and CB/R, a RPLC-purified tryptic peptide derived from a crude mixture of CNBr peptides. The recovery of Pth-amino acid detected in each degradative cycle is indicated in pmoles from which the repetitive yield is calculated. The numbers correspond to various manually collected fractions derived from gradient RPLC, and the lowercase letters correspond to the various manually collected fractions derived from isocratic RPLC, required for further purification.

| Peptide | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 RY[a] |
|---|---|---|---|---|---|---|---|---|---|---|---|---|---|---|---|---|---|---|---|---|---|---|---|---|
| | 25 | 26 | 27 | 28 | 29 | 30 | | | | | | | | | | | | | | | | | | |
| | Gly | Asn | Val | Gly | — | Gln | | | | | | | | | | | | | | | | | | |
| | 16 | 23 | 6 | 15 | | 3 | | | | | | | | | | | | | | | | | | |

[a]Abbreviations: mix, other residues also identified; N/A, not appropriate to calculate a repetitive yield; RY, average repetitive yield; —, no Pth-derivative identified.
[b]Trp indicates that a Pth derivative, eluting in the position of Pth-Trp, was identified at this degradative cycle. Since a Lys reside is found in the protein sequence deduced from the cDNA sequence, Trp is likely to represent a modified form of Lys,m although its chemical structure has not yet been determined.

Example 3—Preparation of Probes

Construction of Probes—Two overlapping, degenerate oligonucleotide probes, YS20.1 and YS17.2 (FIG. 2A), derived from the amino acid sequence of peptide CB18-R11-13c (Table 3) were synthesized and used to screen a rat liver λgt11 cDNA library. The oligonucleotide probes and primers were synthesized with an Applied Biosystems 380A DNA synthesizer using β-cyanoethyl phosporamidites (Sinha, N. D. et al., *Nucl. Acid Res* 12:4539–4557 (1984)) and purified by polyacrylamide gel electrophoresis according to the Applied Biosystems Manual or by ethanol precipitation from a solution of oligonucleotide containing 10 mM $MgCl_2$. YS17.2 and YS20.1 represent pools of 128-fold degenerative oligonucleotides. The YS17.2 and YS20.1 pools were 17 and 20 nucleotides in length, respectively. The two probes overlap by 12 nucleotides, such that sequential use of the probes to screen a DNA library would effectively screen for a 25 nucleotide piece of APH encoded DNA.

Example 4—Creation and Screening of the cDNA Library and Sequencing APH Encoded cDNA Preparation of RNA—Strain CD rat liver was quick-frozen in liquid $N_2$ and thawed in guanidine isothiocyanate, and the RNA was purified by centrifugation through CsCl (Chirgwin et al., *Biochem* 18:5294–5299 (1979)). The yield was 600 μg of RNA. Poly(A)+ RNA was selected by passage of the total RNA through an oligo(dT) cellulose column (Aviv, H. et al., *Proc. Natl. Acad. Sci. (U.S.A.)* 69:1408–1412 (1972)). Forty five μg of poly(A)+ RNA were obtained and shown not to be degraded by RNA blot analysis of 1 μg of RNA by hybridizing with an actin cDNA probe (Spiegelman, B. M. et al., *J. Biol. Chem.* 258:10083– 10089 ((1983)).

Preparation of cDNA Library—Complementary DNA was synthesized from 10 μg poly(A)+ RNA by the method of Gubler, U. et al. (*Gene* 25:263–269 (1983)), and cloned into the λgt11 (Young, R. A. et al., *Proc. Natl. Acad. Sci. (U.S.A.)* 80:1194–1198 (1983)), as described by Klickstein, L. B. (In: *Current Protocols in Molecular Biology* (Ausubel, F. M. et al., Eds.) pp 5.8.1.–5.8.4., Wiley-Interscience and Greene Publishing Associates, New York, N.Y. (1987)). The yield of recombinants was 4 million from 100 ng of cDNA and 10 μg of λgt11 vector DNA. The library was amplified in *E. coli* strain Y1088 (δlacU169, supE, supF, HsdR⁻, HsdM⁺, metB, trpR, tonA21, proC::Tn5 (pMC9)) and stored at 4° C.

Isolation of cDNA Clones—The library was plated at 25,000 plaques per 150 mm plate (for screening $10^6$ or fewer plaques) or at $10^6$ plaques per 225 mm×225 mm plate (for screening more than $10^6$ plaques), and duplicate filters were lifted from each ((Maniatis, T. et al., *Molecular Cloning: A Laboratory Manual,* Cold Spring Harbor Laboratory, Cold Spring Harbor, N.Y. (1982)).

For screening with oligonucleotides, the oligonucleotides were 5' end-labeled to a specific activity of 2–8×$10^8$ cpm/μg with [λ-$^{32}$P]-ATP and T4 polynucleotide kinase (Zoller, M. et al., *DNA* 3:479–488 (1985)). The filters were hybridized with oligonucleotide in 6×SSC, 0.1% SDS, 0.1% SDS, 0.05% sodium pyrophosphate, 1×Denhardt's solution and 100 μg/ml salmon sperm DNA at 65° C. overnight. The $T_{d\ max}$ and $T_{d\ min}$ were calculated for each mixture of oligonucleotides with the formula: $T_d=4(G+C)+2(A+T)$, as previously described for short sequences (Suggs, S. V. et al., In: *Developmental Biology Using Purified Genes* (Brown, D., Ed.), pp. 683–693, Academic Press, New York, N.Y. (1981)). The sequences were washed at progressively higher temperatures in 6×SSC, 0.05% sodium pyrophosphate, and 0.1% SDS until non-specific binding was reduced.

For screening with cDNA probes, (XmnI-KpnI fragment from APH5.2 or BanII-PstI fragment from APH36.1; FIG. 2B) the filters were hybridized overnight with nick-translated probes in 50% formamide, 5×SSC, 5×Denhardt's solution, 10 mM sodium phosphate, 0.1% SDS, 1 mM EDTA and 50 μg/ml sonicated, denatured salmon sperm DNA at 42° C. Filters were washed in 0.2×SSC, 0.1% SDS, 1 mM sodium phosphate, pH 7.0, and 1 mM EDTA at 55° C. The washed filters were exposed to Kodak XAR film with an intensifying screen at −70° C. Phage yielding duplicate signals were plaque-purified by additional rounds of screening.

DNA Sequence Analysis—Restriction fragments from APH5.2 and APH36.1 were subcloned into M13mp18 or M13mp19 and sequenced by the dideoxynucloetide chain termination method (Sanger, F. et al., *J. Molec. Biol.* 94:441–448 (1975)). The sequence of some clones was obtained by first constructing deletion mutants using exonuclease III (Henikoff, S., *Gene* 28:351–356 (1984)). The cDNA insert of APH2.7 was subcloned into Bluescript plasmid (Stratagene) and sequenced by the dideoxy chain termination method, modified for double-stranded sequencing by Guo et al. (*Nucl. Acids Res.* 12:387–394 (1983)). The DNA sequence data were analyzed with the University of Wisconsin Genetics Computer User Group programs (Devereux, J. et al., *Nucl. Acid Res.* 12:387–395 (1984)).

Cloning and Sequencing of cDNA Encoding Rat Liver Acyl-Peptide Hydrolase—Twenty-Seven out of 450,000 recombinant clones were found to hybridize with probe YS20.1. Twelve of these clones were rescreened with the probe, YS17.2 to yield a single clone, APH5.2, containing a 1.3 kb insert (FIG. 2B). The DNA sequence of APH5.2 encoded the entire peptide sequence of the tryptic peptide CB18-R11-13-c confirming that APH5.2 was an authentic clone. Since APH5.2 contained a poly(A)+ sequence at its 5' end (FIG. 2B, cross-hatched box), probably artifactually created during the construction of the cDNA library, an XmnI-KpnI fragment of APH5.2 was used to rescreen one million clones from the same cDNA library, and the APH36.1 clone containing a 2.5 kb insert was obtained (FIG. 2B). The protein sequence deduced from the DNA sequence of APH36.1 contained all of the protein sequences in Table 3, except for the amino terminal three residues of peptide CB17-R13. However, its 5' end contained a 120 bp fragment encoding rat serum albumin (FIG. 2B, box with diagonals).

In order to obtain the missing 5' sequence data, a 220 bp BanII-PstI fragment (FIG. 2B) was used to rescreen the same cDNA library. Five positive clones with different length Poly(A) tails were obtained from 5 million recombinants. Four cDNA clones, including APH2.7, started with the same nucleotide sequence and contained an in-frame ATG codon at nucleotides 6–8, while the 5' end of the fifth cDNA clone lacked 18 base pairs. A polyadenylation signal, AATAAA, was found at nucleotides 2344–2349. FIG. 3 illustrates the complete cDNA sequence for APH, as derived from APH5.2, APH36.1 and APH2.7.

Primary Structure of Acyl-peptide Hydrolase Deduced from cDNA—The complete DNA sequence was determined by combining the sequences of APH36.1 and APH2.7 (FIG. 3). The DNA sequence encodes a protein containing 732 amino acid residues, assuming that the ATG at nucleotides 6–8 is the translation initiation codon. The deduced protein sequence contains all the peptide sequences in Table 3 (FIG. 1). The protein has a calculated molecular weight of 81,347, and the amino acid composition based on the deduced protein sequence agrees closely with the observed composition (Table 2). As deduced from the DNA sequence, three lysyl residues were identified at amino acid residues 118, 291, and 443, which correspond to the positions where Pth-Trp together with a late-eluting Pth-derivative were observed (Table 3 and FIG. 1). Three N-glycosylation consensus sequences (i.e., Asn-Xxx-Thr/Ser (Parodi, A. J. et al., *Biochim. Biophys. Acta* 559:1–37 (1979)) are identified at residues 134–136, 233–235, and 243–245.

Hydrophobicity Analysis—The hydrophobicity profile was determined using the algorithm of Kyte, J. et al. (*J. Molec. Biol.* 157:105–132 (1982)) with a window size of 8.

The deduced protein sequence of rat acyl-peptide hydrolase was compared to the National Biomedical Research Foundation and Swiss protein databases using the Wordsearch and Bestfit programs from the University of Wisconsin Genetics Computer User Group programs (Devereux, J. et al., *Nucl. Acid Res.* 12:387–395 (1984)), and the FASTP program based on the algorithm of Lipman, D. J. et al. (*Science* 227:1435–1441 (1985)). In order to identify possible active site regions in rat acyl-peptide hydrolase, its sequence was compared with the peptide sequences, containing the active-site seryl, histidyl or aspartyl residues, derived from known serine proteases.

The hydrophobicity plot reveals that the protein contains a hydrophilic region located between residues 80 and 220, but it remains unclear whether this region has a specific role in interactions with other proteins or in catalysis. The computer-based search of the National Biomedical Research Foundation and the Swiss Protein databases revealed no strongly homologous proteins. In addition, the comparison between rat acyl-peptide hydrolase and short active site serine-, histidine-, and aspartic acid-containing peptides, derived from known serine proteases, failed to reveal any significant similarities. Although acyl-peptide hydrolase was previously shown to be serine protease by inhibition experiments, using diisopropyl fluorophosphate, acetylalanine chloromethyl ketone, and other enzyme inhibitors (Kobayashi, K. and Smith, J. A., *J. Biol. Chem.* 262:11435–11445 (1987); Tsunasawa et al., *J. Biochem. (Tokyo)* 77:89–102 (1975)), no strong similarity between rat acyl-peptide hydrolase and active-site peptides from other serine proteases were found, suggesting that this enzyme may be a unique serine protease.

Example 4—Cloning of the Entire Rat Acyl-Peptide Hydrolase Gene

Materials—Restriction enzymes, T4 ligase, T4 polynucleotide kinase, *E. coli* DNA polymerase I and its Klenow fragment, AMV reverse transcriptase, exonuclease III, DNase I, RNase H, T4 DNA polymerase, EcoRI methylase, calf intestinal alkaline phosphatase, and nuclease S1 were from Boehringer Mannheim and New England Biolabs. RNase A was from Sigma. The Bluescript plasmid, λgt10 arms and packaging extract were from Stratagene. [λ-$^{32}$P] ATP, [α-$^{32}$P]dCTP, and GeneScreen Plus membrane were purchased from New England Nuclear. [α-$^{35}$S][dATPαS was from Amersham Corp. Oligo(dT)-cellulose was from Collaborative Research. Synthetic oligonucleotides were synthesized with an Applied Biosystems 380A DNA Synthesizer using the silica-based solid phase (Matteucci, M. D. et al., *J. Am. Chem. Soc.* 103:3185–3191 (1981)) and β-cyanoethyl phosphoramidite method (Sinha, N. D. et al., *Nucleic Acids Res.* 12:4539–4544 (1984)).

Preparation of Rat Liver DNA and RNA—The source of rat genomic DNA and liver cytoplasmic RNA is adult Sprague-Dawley rat liver. Liver DNA was prepared as described by Blin and Stafford (Blin, N. et al., *Nucleic Acids Res.* 3:2303–2308 (1976)). Rat liver total RNA was isolated by guanidine thiocyanate method, as described by Chrigwin et al. (Chirgwin, J. M. et al., *Biochemistry* 18:5294–5299 (1979)). Polyadenylated RNA was purified by oligo(dT)-cellulose chromatography (Aviv, H. et al., *Proc. Natl. Acad. Sci. USA* 69:1408–1412 (1972)).

RNA Blot Analysis—RNA was purified as described above, denatured at 65° C. and transferred to Zetabind membrane (Thomas, P. S., *Proc. Natl. Acad. Sci. (U.S.A.)* 77:5201–5202 (1980)). Blots were hybridized with the nick-translated XmnI-KpnI cDNA fragment from APH5.2 in 50% formamide, 5×SSC, 5×Denhardt's solution, 10 mM sodium phosphate, 0.1% SDS, 1 mM EDTA and sonicated, denatured salmon sperm DNA (50 µg/ml). Filters were washed in 0.2×SSC, 0.1% SDS, 10 mM sodium phosphate pH 7.0 and 1 mM EDTA at 55° C.

The RNA blot analysis of total RNA, using the XmnI-KpnI cDNA fragment derived from APH5.2 as probe (FIG. 2B), revealed that a single mRNA of 2.7 kb in roughly equivalent amounts encodes acyl-peptide hydrolase in various rat tissues (i.e., spleen, muscle, lung, liver, kidney, and brain).

Isolation of Genomic Clones—Two rat genomic libraries were used to screened for APH gene. One library was from Clonetech, which was constructed by partial EcoRI digestion of Sprague-Dawley liver DNA and cloning into λ phage Charon 4A. A 2.4 kb EcoRI restriction fragment encoding rat APH derived from APH36.1 was labeled by nick translation (Sargent, T. D. et al., *Proc. Natl. Acad. Sci. USA* 76:3256–3260 (1979)) with [α-$^{32}$P]dCTP to a specific activity of 108 cpm/µg and used as a probe for screening this genomic library. The other library which is constructed by partial HaeIII digestion and cloning into λ phage Charon 4A was a generous gift from Professor James Bonner of California Institute of Technology (Church, G. M. et al., *Proc. Natl. Acad. Sci. USA* 81:1991–1995 (1984)). A 200 bp BanII-PstI fragment of APH36.1 labeled by random-priming (Feinberg, A. et al., *Anal. Biochem.* 132:6–13 (1983)) with [α-$^{32}$P]dCTP to a specific activity of $10^9$ cpm/µg, was used to screen this library. Approximately 1×$10^6$ phages from each library were screened by plaque hybridization (Church, G. M. et al., *Proc. Natl. Acad. Sci. USA* 81:1991–1995 (1984)). Positive plaques were purified, and phage DNA was isolated (Maniatis, T. et al., *Molecular Cloning: A Laboratory Manual*, Cold Spring Harbor Laboratory, Cold Spring Harbor, N.Y. (1982)).

Analysis of DNA by Restriction Mapping and DNA Hybridization—The restriction map of the cloned gene was constructed by digestion of phage DNA with various restriction endonucleases (Maniatis, T. et al., *Molecular Cloning: A Laboratory Manual*, Cold Spring Harbor Laboratory, Cold Spring Harbor, N.Y. (1982)). For DNA blot analysis, DNA restriction fragments were separated in an agarose gel, blotted onto GeneScreen Plus membrane, and hybridized to $^{32}$P-labeled probe according to manufacturer's recommendations. Probes are three $^{32}$P-labeled rat APH cDNA fragments of APH36.1: a 5' 200 bp BanII-PstI fragment, a 420 bp Kpn-EcoRI fragment, and a 2.4 kb EcoRI fragment. For genomic DNA blot hybridization, the 2.4 kb EcoRI fragment of APH2.7 was used as the probe.

DNA Sequencing—Restriction fragments of the rat genomic clones were subcloned into Bluescript plasmid. Both orientations of the complete sequence, as well as upstream and downstream regions, of the rat APH gene were determined by Sanger's dideoxy chain termination method (Sanger, F. et al., *Proc. Natl. Acad. Sci. USA* 74:5463–5467 (1977)), modified for double-stranded sequencing (Guo, L.-H. et al., *Nucleic Acids Res.* 11:5521–5539 (1983)), employing sequencing strategies of the DNase I deletion method (Lin, H.-C. et al., *Anal. Biochem.* 147:114–119 (1985)), exonuclease III deletion method (Henikoff, S., *Gene* 28:351–359 (1984)), and synthetic oligonucleotide primers. Nucleotide sequence data were compiled and analyzed by the Genetics Computer Group Sequence Analysis Software Package, version 5.0 (Devereux, J. et al., *Nucleic Acids Res.* 12:387–395 (1984)).

Preparation of a cDNA Library Containing 5'-Untranslated Region of APH mRNA—A 17 bp synthetic oligonucleotide, 5' GTGACCTCCGGACCCAG 3', complementary to nucleotides 95–112 of the APH2.7 was used as a specific primer to construct a cDNA library in λgt10. The synthetic oligonucleotide (1 μg) was annealed to 10 μg of poly(A)⁺RNA, and the first and second strand synthesis of the cDNA was performed by the method of Gubler and Hoffman (Gubler, U. et al., *Gene* 25:263–269 (1983)). The ends of cDNAs were blunted with T4 DNA polymerase, and internal EcoRI sites were methylated. The blunt-ended cDNAs were ligated to EcoRI linkers, and following EcoRI digestion the cDNAs were size-fractionated on a CL-4B column (Wong, W. W. et al., *Proc. Natl. Acad. Sci. USA* 82:7711–7715 (1985)). Then the cDNAs were ligated to λgt10 arms, and the recombinant phage DNA was packaged according to the manufacturer's (Stratagene) recommendations. Recombinant phages were screened with 2 synthetic oligonucleotides, 5' AAGTCCCG-GAAGTGAGG 3' and 5' CTGACGCTCCATAGTCG 3', whose sequences were derived from genomic (nucleotides 586–592, FIG. 4A) and cDNA sequence (nucleotides 1–17 of APH2.7) respectively. The phage DNA with the largest insert was purified (Maniatis, T. et al., *Molecular Cloning: A Laboratory Manual,* Cold Spring Harbor Laboratory, Cold Spring Harbor, N.Y. (1982)), and the insert was subcloned into Bluescript plasmid.

Primer Extension—An oligonucleotide, 5' TAGGAGT-GAGAAAATCA 3', complementary to nucleotide sequence in the first exon (nucleotides 44–60, FIG. 4A) was labeled at 5' end with [λ-³²P]ATP and T4 polynucleotide kinase and then hybridized to 10 μg of rat liver poly(A)⁺RNA in a solution of 0.1M KCl, 5 mM EDTA, a nd 5 mM sodium phosphate, pH 6.8. For hybridization, the temperature of the solution was raised to 90° C. for 5 min and returned gradually to 42° C. The RNA-DNA hybrids were then subjected to reverse transcriptase reaction. After RNase A digestion, phenol:chloroform extraction, and ethanol precipitation, the primer extension product was then electrophoresed on an 8% polyacrylamide sequencing gel.

Figure 5A:
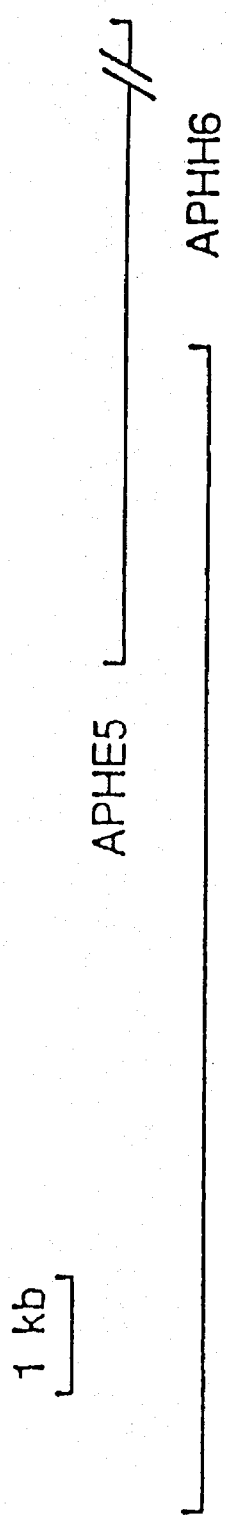
FIGS. 5A–C show a structural organization of the rat acyl-peptide hydrolase gene.
Figure 5B:
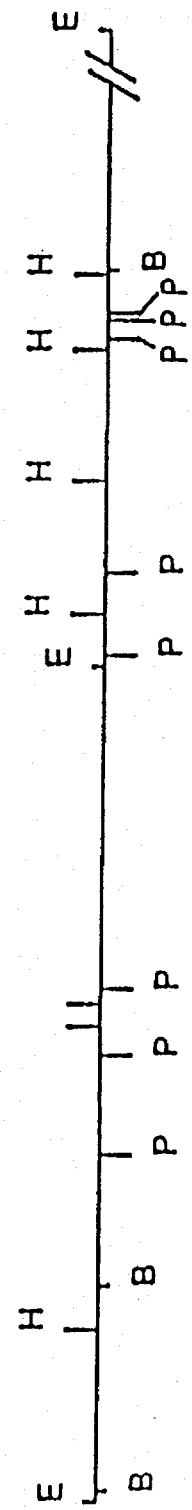

Isolation and DNA Sequence of the Rat Acyl-peptide Hydrolase Gene—Initially, a rat genomic library, constructed in Charon 4A from a partial EcoRI digest of Sprague-Dawley rat liver DNA was screened using the ³²P-labeled rat liver APH cDNA insert of APH36.1, as the probe. One million plaques were screened, and twenty-eight hybridized with the probe. All twenty-eight plaques were isolated and characterized by restriction enzyme mapping and were found to be identical. DNA blots of the restriction endonuclease digests derived from each recombinant DNA were probed with the cDNA inserts of APH36.1, the 200 bp BanII-PstI fragment (5' end of APH36.1), and the 420 bp KpnI-EcoRI fragment (3' end of APH36.1), and each contained a 9.7 kb EcoRI fragment, corresponding to the 3' end of the cDNA. One of these clones, APHE5 (FIG. 5A), was restriction enzyme-mapped, subcloned into Bluescript, and sequenced. A second rat genomic library, constructed by partial HaeIII digestion of rat liver DNA and cloned into Charon 4A (generously provided by Professor J. Bonner, California Institute of Technology), was screened with the 200 bp BanII-PstI fragment of APH36.1. Eight of one million plaques hybridized with the probe, and their phage DNAs were isolated. After restriction enzyme-mapping and DNA hybridization, one clone, APHH6 (FIG. 5A), overlapping with clone APHE5 and extending further in the 5' direction was analyzed. The combined restriction map of APHE5 and APHH6 is shown in FIG. 5B.

DNA blot analysis of rat genomic DNA revealed two bands corresponding to BamHI restriction fragments of about 4 and 9.4 kb. The size of the larger fragment agrees with the size calculated from the restriction map, and the smaller fragment extends beyond the 3' end of the map (FIG. 5B). Two bands corresponding to EcoRI restriction fragments of about 7.5 and 9.7 kb were observed. The sizes of both fragments agree with the sizes determined from the restriction map (FIG. 5B). This indicates that APH gene is present in a single form in the rat genome.

Figure 5C:
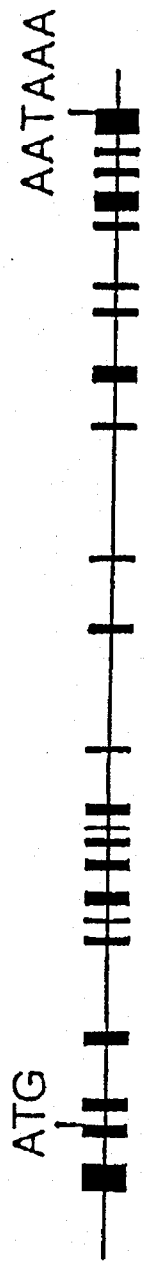

For sequence analysis, the individual EcoRI, PstI or BamHI fragments were subcloned into Bluescript, and individual subclones were either subjected to limited unidirectional digestion with exonuclease III followed by S1 nuclease digestion or subjected to random, limited nicking with DNase I followed by restriction enzyme digestion to generate a nested set of deletions. Double-stranded plasmid DNA was prepared from each deletion and sequenced by the dideoxy chain termination method. For certain regions, the sequence was determined by using specific synthetic oligonucleotides as the sequencing primers. These two genomic clones were sequenced in both orientations. The complete nucleotide sequence is shown in FIGS. 4 and 4A–4E. For simplicity in discussing the genomic sequence, a numbering system is used in which position +1 denotes the transcriptional initiation site of the APH gene. As shown in FIG. 5C and Table 4, the precise locations of each of the 5' and 3' exon-intron boundaries were defined by aligning the genomic sequence with the cDNA sequence.

Analysis of the 5'-Untranslated Region of Rat Acyl-peptide Hydrolase mRNA—Because the cDNA sequence lacked about 300 base pairs of the 5'-untranslated region, estimated by comparing the size of APH mRNA and the size of cDNA, a cDNA library containing the 5'-untranslated region of APH mRNA was constructed as described above.

Figure 4A:
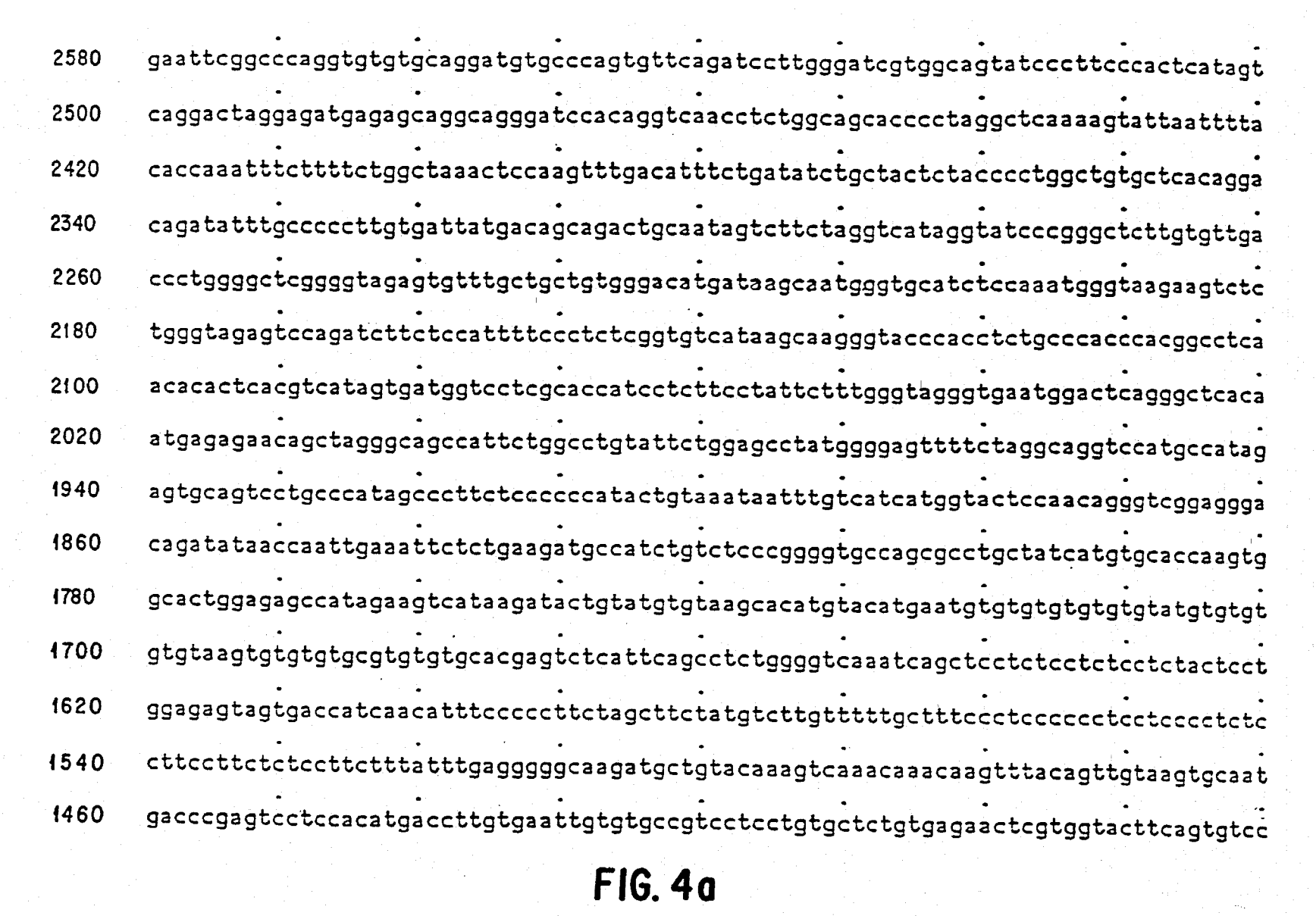

This library was screened with two ³²P-labeled oligonucleotide probes with sequences complementary to the first seventeen bases of the cDNA clone APH2.7 or to nucleotides 586–602 of the genomic DNA (FIG. 4A). A 466 bp cDNA insert was isolated, subcloned into Bluescript, and sequenced by the dideoxy chain termination method. This 5'-extension sequence contained the nucleotide sequence corresponding to nucleotides 37 to 262, 492 to 636, and 711 to 805 of the genomic DNA (FIG. 4A). Therefore, the translational initiation codon, ATG, is located at nucleotides 625–627 (FIG. 4A) since it is preceded in frame by a termination codon, TAG, at nucleotides 568–570 and since there is no other ATG codon in between.

TABLE 4

Intron-Exon Junctions in the Acyl-Peptide Hydrolase Gene

| exon no. | size of exon | 5' splice site | 3' splice site | intron size (bp) |
|---|---|---|---|---|
| 1 | 262 | GCTCACAgtcggct | ccccagCTGGTTG | 229 |

TABLE 4-continued

Intron-Exon Junctions in the Acyl-Peptide Hydrolase Gene

| exon no. | size of exon | 5' splice site | 3' splice site | intron size (bp) |
|---|---|---|---|---|
| 2 | 145 | GCGTCAGgtgaggg-----tgcgcagGTGCTGC | | 74 |
| 3 | 133 | CACACTGgtgtgta-----cttgcagAGTGGAC | | 452 |
| 4 | 127 | GGGGGGAgtaagtg-----ttctcagGCTGCTG | | 746 |
| 5 | 94 | CTTGGAGgtgagtc-----tcctcagGTCTGGG | | 92 |
| 6 | 76 | GAGGATGgtgaggc-----catgtagACTGCTT | | 89 |
| 7 | 164 | CATCAAGgtgcttg-----ttctcagGGGGACC | | 141 |
| 8 | 138 | TGGTCAGgtcagca-----tttacagGCTTTTT | | 94 |
| 9 | 92 | ATCGCAGgtgagga-----tttccagATCAGCT | | 76 |
| 10 | 41 | AAGTGTGgtaagtg-----ggcctagAACTACT | | 91 |
| 11 | 122 | CTGCCTGgtgagtt------cttcagTACGACT | | 462 |
| 12 | 61 | CTGGGAGgtaagag-----tttgcagAGAGCTT | | 1003 |
| 13 | 98 | TCGGCAGgtaaaag-----gtttaagGACCTGT | | 601 |
| 14 | 52 | ACAGCTGgtgagca-----cctctagCGGGGTC | | 1104 |
| 15 | 89 | AAGCCTGgtgagta-----ttggcagAAAGTTG | | 358 |
| 16 | 139 | CAATATGgtgagct-----cctgcagCTGACCT | | 411 |
| 17 | 84 | CCCCATGgtaggta-----tctgcagGGGGACC | | 148 |
| 18 | 81 | CTTCTGGgtaatgc-----ctttcagTGAACTA | | 454 |
| 19 | 89 | TGTCCAGgttgcag-----actttagTTTGCAG | | 93 |
| 20 | 191 | CTGATTGgtgagtg-----tttatagGTGTATG | | 84 |
| 21 | 103 | CCCTCAGgtactca-----tacccagGTAAAGA | | 87 |
| 22 | 107 | CTGTCCGgtgagtg-----cacatagGCTCCTG | | 85 |
| 23 | 262 | | | |

Determination of the Translational Initiation Site of the Rat Acyl-peptide Hydrolase Gene—The 5' end of the APH mRNA was mapped by primer extension analysis. A $^{32}$P-labeled oligonucleotide, 5' TAGGAGTGAGAAAATCA 3', complementary to nucleotides 44–60 (FIG. 4A), was hybridized with rat liver poly(A)$^+$ RNA. This primer was extended with reverse transcriptase in the presence of deoxynucleotides, and the length of the extended product, determined as described above, was 60 nucleotides. Furthermore, if yeast poly(A)$^+$ RNA was substituted for rat liver poly(A)$^+$ RNA, no extended product was observed. Transcription was found to begin with a T residue on the DNA template, which corresponds to an A residue at position 1 in FIG. 4A. This A residue is situated 395 bp 5' of the ATG translational initiation codon.

In summary, these examples show that the rat APH gene is present in a single form. The complete sequence of the rat APH gene was determined, including 2.58 kb of 5' flanking DNA, 2.75 exonic DNA, 6.94 kb of intronic DNA, and 1 kb of 3' flanking DNA (FIGS. 4 and 4A–4E). The exonic DNA data unequivocally identified the translational initiation site, corresponding the codon encoding the methionine at residue 1 of rat acyl-peptide hydrolase, since there was no ATG codon positioned between the in frame stop coding (FIGS. 4 and 4A–4E, nucleotides 568–570) and the translational initiation codon in exon 2 (FIGS. 4 and 4A–4E).

These results also indicate that APH is not synthesized as a precursor protein, since the protein sequence of APH following the NH$_2$-terminal Met could be identified by automated Edman degradation following CNBr cleavage.

As shown in FIG. 5C, rat APH gene, spanning 9.69 kb is divided into 23 exons. The individual exons vary in size between 41 and 262 bp (Table 4). The first intron interrupts the 5'-untranslated sequence; all of the other introns were within the protein coding region of the gene. Table 4 lists the sequences at the 5' and 3' junctions of each intron, and these sequences are consistent with the consensus sequences for intron-exon junctions of other eukaryotic genes (Sharp, P. A., *Cell* 23:643–646 (1981); Breathnach, R. et al., *Annu. Rev. Biochem.* 50:349–383 (1981); Mount, S. M., *Nucleic Acids Res.* 10:459–472 (1982)). All introns begin with the sequence GT at the 5' boundary and end with the sequence AG to the 3' boundary, and in all cases the intron sequences flanking the 5' and 3' boundaries are purine and pyrimidine-rich, respectively. The exon-intron organization of APH gene, presumably encoding a protease with active-site serine residue (Kobayashi, K. and Smith, J. A., *J. Biol. Chem.* 262:11435–11445 (1987)), is much more complex than either trypsin or chymotrypsin, which contain five and seven exons, respectively (Rogers, J., *Nature* 315:458–459 (1985)). The residues of the charge relay systems of these enzymes are known to be encoded by separate exons, but the distribution of the corresponding residues in APH awaits additional studies. Based on an extensive search of the National Biomedical Research Foundation and Swiss Protein databases, as well as a comparison of exon-intron organization of other serine proteases (e.g., trypsin, chymotrypsin, elastase, urokinase, kallikrein, adipsin), acyl-peptide hydrolase is not clearly similar to any of these serine proteases.

Analysis of the 5' flanking DNA of the APH gene revealed a number of conserved sequences. These is a sequence 5' TGATAAA 3' which could be a variant sequence for a "TATA" box, located at nucleotides −24 to −30. This is a customary location for the TATA box, which is typically found 26–34 nucleotides upstream from the transcriptional initiation site (Cordon, J. et al., *Science* 209:1406–1414 (1980)). Another sequence, 5'-TCAAT-3' (nucleotides −95 to −99), is found 95 nucleotides upstream from the transcriptional initiation site and is similar to the "CCAAT" box sequence, which is usually found 70–80 bases from the transcriptional initiation site. In addition, a 6 bp sequence, GGGCGG, is repeated three times. One repeat is located at the positions −81 to −76 and is presumed to be within the promoter region of the APH gene. The other two repeats, present in the reverse orientation as CCGCCC, are located 5 nucleotides and 31 nucleotides downstream from the transcriptional initiation site. It is reported that all the Sp1-binding regions contain one or more exact copies of this GGGCGG sequence, which may be present in either orientation with respect to transcription (Dynan, W. S. et al., *Nature* 316:774–448 (1985)).

A 200 bp sequence appears tandemly starting at 917 bp upstream from the transcriptional initiation site. Compared with other sequences in the gene bank, the 3' two-thirds of this sequence is similar to the mouse type 2 Alu repeat (80% in similarity) (Kominami, R. et al., *J. Mol. Biol.* 165:209–228 (1983)). A similar sequence, but only as one copy, is present in the junction of SV40 and Fisher rat DNA (Hasson, J.-F. et al., *J. Mol. Biol.* 177:53–68 (1984)) and several other genes (Min, H. Y. et al., *Nucleic Acids Res.* 14:8879–8892 (1986); Osumi, T. et al., *J. Biol. Chem.* 262:8138–8143 (1987); Corden, L. J. et al., *Proc. Natl. Acad. Sci. USA* 82:7934–7938 (1985); Phillips, M. et al., *J. Biol. Chem.* 261:10821–10827 (1986)). This repeat may have a regulatory role.

This gene may be specifically regulated by either cis- and/or trans-acting regulatory factors. Such regulation may be associated with protein synthesis or degradation.

Acyl-peptide hydrolases have been isolated from various mammalian tissues, and their molecular properties and reaction mechanism have been partially characterized. One aspect of the present invention concerns the primary structure of rat liver acyl-peptide hydrolase which has been deduced from the nucleotide sequence of two cDNA clones isolated from a rat liver λgt11 library (FIG. 3). This cDNA encodes a protein of 732 amino acid residues, and protein sequence analyses derived from 19 CNBr and tryptic peptides confirmed the identity of 292 residues. This enzyme has been shown to consist of 4 subunits of identical size based on estimations of $M_r$ for the native protein and its subunits by gel filtration and SDS-PAGE, respectively (Kobayashi, K. and Smith, J. A., *J. Biol. Chem.* 262:11435–11445 (1987)). Since all the peptide sequences obtained were found in the deduced protein sequence, it is likely that the four subunits are identical in their primary structure. A comparison of the deduced protein sequence (FIG. 1) and the amino acid sequences derived from automated Edman degradation (Table 3) reveals that the protein contains three equivalently modified lysyl residues (residues 118, 291, 443), although the chemical nature of this modification has not yet been determined.

There are three indirect lines of evidence that suggest that the methionine residue at position 1 is indeed the $NH_2$-terminus of the protein. First, the calculated molecular weight agrees closely with the subunit $M_r$ estimated by SDS-PAGE (81,347 versus 80,000 (Kobayashi, K. and Smith, J. A., *J. Biol. Chem.* 262:11435–11445 (1987)), respectively). Second, the theoretical amino acid composition is similar to the observed amino acid composition of purified acyl-peptide hydrolase (Table 2). Third, the initiation codon, ATG, corresponding to this methionine is in the right context for an initiation codon, as described by Kozak, M. (*Cell* 44:283–292 (1986)).

The $NH_2$-terminal sequence of the deduced primary structure of the enzyme is Met-Glu-Arg-Gln . . . . However, previous protein sequence analysis indicated that the $NH_2$-terminus of the protein is blocked (Kobayashi, K. and Smith, J. A., *J. Biol. Chem.* 262:11435–11445 (1987)). If the methionine were removed during translation by a methionine-specific aminopeptidase, a residue located more C-terminally would be expected to be blocked, in which case the sequence of peptide CB17-R13 (Glu-Arg-Gln . . . ) could not be obtained. Therefore, the methionine residue remains on the polypeptide chain and undergoes an $NH_2$-terminal modification. Although the chemical nature of this blocking group has not yet been established, the well-documented occurrence of glutamyl residues, as well as aspartyl and asparaginyl residues adjacent to acetylated methionines suggests that the protein probably is $N^\alpha$-acetylated. If this is the case, the Ac-Met of acyl-peptide hydrolase is apparently not cleaved in vitro or in vivo by itself or other $NH_2$-terminal processing enzymes during its processing or intracellular sorting.

It has been demonstrated that acyl-peptide hydrolase does not effectively remove an acetylated amino acid from native or denatured proteins in vitro (Kobayashi, K. and Smith, J. A., *J. Biol. Chem.* 262:11435–11445 (1987); Gade et al. *Biochim. et Biophys. Acta* 662:86–93 (1981)), although such residues are effectively cleaved from $N^\alpha$ acetylated peptides (<20 residues). Therefore, it seems likely that the in vivo substrates for this enzyme may be short $N^\alpha$-acetylated peptides resulting from protein degradation. However, a role for this enzyme in the removal of $N^\alpha$-acetylated amino acids from other polypeptide chains during co-translational processing cannot be ruled out (Rubenstein, P. A. et al., *J. Biol. Chem.* 258:11354–11360 (1983)).

RNA blot analysis indicates that a single 2.7 kb RNA encodes acyl-peptide hydrolase in all the rat tissues examined. Further, the amount of mRNA detected in these tissues appears to be roughly equivalent, suggesting that there are no tissue-specific regulation of acyl-peptide hydrolase mRNA levels.

Example 5—Detection and Diagnosis of Small Cell Carcinoma

Four major types of lung neoplasms—small cell carcinoma (also referred to as "oat cell" carcinoma), squamous carcinoma (also referred to as epidermoid carcinoma), adenocarcinoma and large cell carcinoma—account for 95% of all primary lung neoplasms. Small cell carcinoma is of substantial medical importance. It accounts for about 25% of all lung neoplasms. Whereas other forms of lung cancer have 27–37% 5-year survival times, less than 1% of patients suffering from small cell carcinoma survive 5 years from the time of diagnosis (See, for example, Harrison's Principles of Internal Medicine, 11th Ed., Braunwald, E. et al., eds. (1987), pp.1115–1123, which reference is incorporated herein by reference).

Presently, small cell carcinoma is generally detected through routine chest radiograph; as many as 5–15% of such cancers are asymptomatic at the time of detection. The disease is said to be in a limited stage when it is confined to one hemithorax and regional lymph nodes; the disease is said to be in an extensive stage when greater involvement is observed.

Early detection of small cell Carcinoma is associated with a substantial increase in prognosis. Five year cure rates for limited stage disease are potentially 15–25%, however, the potential 5 year cure rate for extensive stage disease is only 1–5%.

Small cell carcinoma is treated with intensive chemotherapy and radiotherapy. The initial goal of treatment is to obtain a complete regression of the tumor within 6–12 weeks of therapy. Although the tumor often returns, the extent of regression correlates to both median and long-term survival. Because of its metastatic potential, small cell carcinoma is not generally treatable with surgery. However, if detected at an early stage, surgical resection is possible, and is associated with significantly improved cure rates.

Karyotypic studies have revealed a consistent deletion in chromosome 3p (p14–p23) among small cell carcinomas (Whang-Peng, J. et al., *Science* 215:181–182 (1981)). This observation has been supported by polymorphic RFLP marker studies (Naylor, S. L. et al., *Nature* 329:451–454 (1987); Kok, K. et al., *Nature* 330:578–581 (1987); Brauch, H. et al., *N. Engl. J. Med.* 317:1109–1113 (1987); Yakota, J. et al., *Proc. Natl. Acad. Sci. (U.S.A.)* 84:9252–9256 (1987)). The frequency of allele loss indicates that virtually all small cell carcinomas contain a deletion for a portion of chromosome 3 (Naylor, S. L. et al., *Genomics* 5:355–361 (1989), which reference is incorporated herein by reference).

The short arm of chromosome 3 has been implicated in other lung cancers, in renal cell carcinomas, and in von Hippel-Lindau syndrome (Kok, K. et al., *Nature* 330:578–581 (1987); Brauch, H. et al., *N. Engl. J. Med.* 317:1109–1113 (1987); Zbar, B. et al., *Nature* 327:721–724 (1987); Kovacs, G. et al., *Proc. Natl. Acad. Sci. (U.S.A.)* 85:1571–1575 (1988); Seizinger, B. R. et al., *Nature* 332:268–269 (1988), which references are incorporated herein by reference. The loss of activity of aminoacylase 1 in small cell carcinoma tumors and the familial association of some of these diseases further supports the correlation between these diseases and a deletion in the small arm of chromosome 3 (Naylor, S. L. et al., *Genomics* 5:355–361 (1989)).

Recently, a DNA sequence (designated "DNF 15S2") was cloned, and mapped to chromosome 3 (Gerber, M. J. et al., *Amer. J. Hum. Genet.* 43:442–451 (1988), which reference is incorporated herein by reference; Naylor, S. L. et al.,

*Genomics* 4:355–361 (1989)). The cloned DNA was found to be capable of identifying RFLP differences between normal DNA and DNA of small cell carcinomas- In particular, polymorphisms were identified using the TaqI restriction enzyme.

The amino acid sequence of the acyl-peptide hydrolase of the present invention is substantially similar to the amino acid sequence encoded by the DNF 15S2 probe sequence. Of the 621 residues of the DNF 15S2 protein, 67.6% were identical to those found in the acyl-peptide hydrolase of the present invention (FIG. 6). Thus, nucleotide sequences which encode the acyl-peptide hydrolase of the present invention, or fragments of this enzyme, may be used as probes to detect and identify small cell carcinoma, and other cancers associated with a deletion in chromosome 3.

When used as a probe, such sequences are incubated under conditions which permit them to hybridize to DNA or RNA of a patient being tested to determine the presence of small cell carcinoma. Suitable hybridization methods are well-known in the art (see, for example, Hames, B. D. and Higgins, S. J. *Nucleic Acid Hybridization, a practical approach,* IRL Press, Washington, D.C. (1985), which reference is incorporated herein by reference.

After hybridization has been achieved, well-known methods for detecting polymorphism (preferably restriction fragment length polymorphism ("RFLP") analysis) may be employed to determine whether a nucleic acid-containing sample contains a polymorphism or sequence which is correlated to the presence of small cell or other carcinoma. Many methods for performing polymorphism detection analysis are known, and may be readily adapted to employ the acyl-peptide hydrolase encoding sequences of the present invention in the detection of small cell and other cancers (see, for example, Wainscoat, J. S. et al., *Hum. Genet.* 75:384–387 (1987); Rabin, D. et al., *Hum. Genet.* 75:120–122 (1987); Azuma, C. et al., *Amer. J. Obstet. Gynecol.* 160:734–736 (1989); Pakkala, S. et al., *Leuk. Res.* 12:757–762 (1988); Todd, S. et al., *Genomics* 4:53–59 (1989); Chowdhury, M. K. U. et al., *Theor. Appl. Genet.* 76:25–32 (1988); Yam, P. et al., *Amer. J. Hum. Genet.* 41:867–881 (1987); Freeman, S. M. et al., *Hum. Immunol.* 20:1–12 (1987); Yoffe, G. et al., *Exper. Hematol.* 15:725–728 (1987); Jones, F. S. III et al., *Gene* 39:77–84 (1986); Bernheim, A. et al., *Proc. Natl. Acad. Sci. (U.S.A.)* 80:7571–7575 (1983); which references are incorporated herein by reference).

Polymorphism detection assays have been used to detect and identify cancers (Wada, M. et al., *Jpn. J. Canc. Res.* 78:780–784 (1987); Naylor, S. L. et al., *Genomics* 4:355–361 (1989); Gerber, M. J. et al., *Amer. J. Hum. Genet.* 43:442–451 (1988); Kakehi, Y. et al., *Int. J. Cancer* 43:391–394 (1989); Gum, J. R. et al., *J. Biol. Chem.* 264:6480–6487 (1989), which references are incorporated herein by reference). Such assays may be used as a general model for the assays of the present invention.

Although the foregoing refers to particular preferred embodiments, it will be understood that the present invention is not so limited. It will occur to those ordinarily skilled in the art that various modifications may be made to the disclosed embodiments and that such modifications are intended to be within the scope of the present invention.

What is claimed is:

1. A purified nucleic acid molecule which contains a genetic sequence encoding the amino acid sequence shown in FIG. 3.

2. The purified nucleic acid molecule of claim 1, wherein said molecule is DNA, and wherein said genetic sequence is the nucleic acid sequence of FIGS. 3 or 4.

3. The purified nucleic acid molecule of any of claims 1 or 2, wherein said molecule is cDNA.

4. The purified nucleic acid molecule of any of claims 1 or 2, wherein said molecule is genomic DNA.

5. The purified nucleic acid molecule of any of claims 1 or 2 wherein said molecule is a vector.

6. The purified DNA molecule of claim 5, wherein said molecule is DNA, and wherein said vector is a plasmid.

7. A host transformed with the purified nucleic acid molecule of any of claims 1 or 2.

8. A host according to claim 7 which is a bacterium.

9. A host according to claim 7 which is a yeast.

10. A host according to claim 7 which is a mammalian cell.

11. A purified DNA molecule, wherein said molecule comprises a nucleic acid sequence, said nucleic acid sequence
   1) encoding a naturally occurring mammalian acyl-peptide hydrolase protein, and
   2) wherein said nucleotide sequence hybridizes to a cDNA probe complementary to the nucleotide sequence of FIG. 3 or FIG. 4 when the hybridization is performed at about 42° C. in a medium consisting essentially of 50% formamide, 5×SSC, 5×Denhardt's solution, 10 mM sodium phosphate, 0.1% SDS, 1 mM EDTA and 50 µg/ml of salmon sperm DNA, and wherein washing occurs in a medium consisting essentially of 0.2×SSC, 0.1% SDS, 1 mM sodium phosphate, pH 7.0 and 1 mM EDTA at about 55° C.

12. A purified DNA molecule encoding a naturally occurring mammalian acyl-peptide hydrolase protein, said DNA molecule prepared by a process comprising
   1) hybridizing a cDNA probe to the desired DNA molecule wherein said cDNA probe is complementary to the nucleotide sequence of FIG. 3 or FIG. 4, wherein the hybridization is performed as claimed in claim 11; and
   2) selecting those DNA molecules that hybridize to the cDNA probe.

13. A method of cloning a DNA molecule that encodes a naturally occurring mammalian acyl-peptide hydrolase protein comprising
   1) hybridizing a cDNA probe complementary to the nucleotide sequence of FIG. 3 or FIG. 4 to said DNA molecule, wherein the hybridization is performed at about 42° C. in a medium consisting essentially of 50% formamide, 5×SSC, 5×Denhardt's solution, 10 mM sodium phosphate, 0.1% SDS, 1 mM EDTA and 50 µg/ml sonicated denatured salmon sperm and washing occurs in a medium consisting essentially of 0.2×SSC, 0.1% SDS, 1 mM sodium phosphate, pH 7.0 and 1 mM EDTA at 55° C.;
   2) selecting those DNA molecules that hybridize to said cDNA probe; and
   3) cloning said DNA molecule of part (2).

\* \* \* \* \*